United States Patent
Morimoto et al.

(10) Patent No.: US 10,155,804 B2
(45) Date of Patent: Dec. 18, 2018

(54) COMPOSITION FOR INDUCING DIFFERENTIATION

(71) Applicant: Kinki University, Osaka (JP)

(72) Inventors: Koichi Morimoto, Kinokawa (JP); Saori Kunii, Kinokawa (JP); Ei Yamamoto, Kinokawa (JP); Hiroyuki Ito, Kinokawa (JP); Yoshinori Kuboki, Sapporo (JP)

(73) Assignee: Kinki University, Osaka (JP)

( * ) Notice: Subject to any disclaimer, the term of this patent is extended or adjusted under 35 U.S.C. 154(b) by 40 days.

(21) Appl. No.: 15/307,441

(22) PCT Filed: Apr. 30, 2015

(86) PCT No.: PCT/JP2015/063045
§ 371 (c)(1),
(2) Date: Oct. 28, 2016

(87) PCT Pub. No.: WO2015/167004
PCT Pub. Date: Nov. 5, 2015

(65) Prior Publication Data
US 2017/0051043 A1 Feb. 23, 2017

(30) Foreign Application Priority Data
Apr. 30, 2014 (JP) .................... 2014-094286

(51) Int. Cl.
- C07K 14/78 (2006.01)
- A61K 38/17 (2006.01)
- A23J 3/06 (2006.01)
- A23J 3/34 (2006.01)
- C12P 21/06 (2006.01)

(52) U.S. Cl.
CPC ............. *C07K 14/78* (2013.01); *A61K 38/17* (2013.01); *A23J 3/06* (2013.01); *A23J 3/34* (2013.01); *C12P 21/06* (2013.01)

(58) Field of Classification Search
CPC .................................................... C07K 14/78
See application file for complete search history.

(56) References Cited

U.S. PATENT DOCUMENTS

| 2009/0299034 A1* | 12/2009 | Cejas ................. | C07K 14/78 530/324 |
| 2012/0116053 A1* | 5/2012 | Mirochnitchenko .. | C07K 14/78 530/350 |
| 2014/0044948 A1 | 2/2014 | Tanaka et al. | |

FOREIGN PATENT DOCUMENTS

| JP | 11-012192 A | 1/1999 |
| JP | 2001-031586 A | 2/2001 |
| JP | 2001-103992 A | 4/2001 |
| JP | 2012-120529 A | 6/2012 |
| WO | 2004/020470 A1 | 3/2004 |
| WO | 2012/070679 A1 | 5/2012 |

OTHER PUBLICATIONS

English translation of International Preliminary Report on Patentability issued in corresponding International Application No. PCT/JP2015/063045, dated May 17, 2016, 6 pages.
K. Morimoto et al., Bioscience, Biotechnology, and Biochemistry, vol. 68, pp. 861-867, 2004.
S. Kunii et al., Journal of Biological Chemistry, vol. 285, No. 23, pp. 17465-17470, Jun. 4, 2010.
Sato, K. et al., "Possible involvement of . . . " Journal of Biological Chemistry, Aug. 18, 2000, vol. 275, No. 33, pp. 25870-25875.
The International Search Report issued in corresponding International Application No. PCT/JP2015/063045, dated Jul. 7, 2015, 2 pages.
International Search Report and Written Opinion issued in corresponding International Application No. PCT/JP2015/063045, dated Jul. 8, 2015, 11 pages.
International Preliminary Report on Patentability issued in corresponding International Application No. PCT/JP2015/063045, dated May 17, 2016, 6 pages.
N. Kuznetsova et al., "Does the Triple Helical Domain of Type I Collagen Encode Molecular Recognition and Fiber Assembly while Telopeptides Serve as Catalytic Domains?", The Journal of Biological Chemistry, 274(51), pp. 36083-36088 (1999).
S. Perumal et al., "Collagen fibril architecture, domain organization, and triple-helical conformation govern its proteolysis", PNAS, 105(8), pp. 2824-2829 (2008).
G. Rosenblum et al., "Direct Visualization of Protease Action on Collagen Triple Helical Structure", PLoS One, 5(6), pp. 1-9 (2010).
J. Lauer-Fields et al., "Hydrolysis of Triple-helical Collagen Peptide Models by Matrix Metalloproteinases", The Journal of Biological Chemistry, 275(18), pp. 13282-13290 (2000).
P. Panwar et al., "Effects of Cysteine Proteases on the Structural and Mechanical Properties of Collagen Fibers", The Journal of Biological Chemistry, 288(8), pp. 5940-5950 (2013).
The extended European Search Report dated Oct. 30, 2017 in corresponding EP Application No. 15785722.8.
Office Action issued in corresponding Japanese Application Ser. No. 2016-516419, dated Jan. 24, 2017, 7 pages.

* cited by examiner

*Primary Examiner* — Karen Cochrane Carlson
(74) *Attorney, Agent, or Firm* — Mintz Levin Cohn Ferris Glovsky and Popeo, P.C.; David G. Conlin; Joohee Lee

(57) ABSTRACT

To provide a differentiation-inducing composition and a method for producing the differentiation-inducing composition, the present disclosure describes use of a degradation product containing at least a portion of the triple helical domain of collagen or atelocollagen.

2 Claims, 19 Drawing Sheets
Specification includes a Sequence Listing.

COMPOSITION FOR INDUCING DIFFERENTIATION

CROSS REFERENCE TO RELATED APPLICATIONS

This application is the U.S. national stage pursuant to 35 U.S.C. § 371, of Japanese International Application Ser. No. PCT/JP2015/063045, filed Apr. 30, 2015 and published in Japanese on Nov. 5, 2015 as publication WO2015/167004 A1, which claims the benefit of Japanese Patent Application Serial No. 2014- 094286, filed Apr. 30, 2014, the entire contents of which are hereby incorporated by reference in their entirety.

TECHNICAL FIELD

The present invention relates to a differentiation-inducing composition.

BACKGROUND ART

Collagen is a protein included in the dermis, ligament, tendon, bone, cartilage, and the like, and is a main component of extracellular matrices of multicellular organisms. Advances in research have revealed that collagen has various physiological functions. There is still ongoing research for discovery of new physiological functions and new uses of collagen molecules.

Research has so far revealed that a single collagen molecule is made up of three polypeptide chains, which form a helical structure to constitute a collagen molecule.

That domain of each polypeptide chain which forms a helical structure is called triple helical domain, which has a characteristic amino acid sequence. Specifically, the triple helical domain has repeated occurrences of an amino acid sequence represented as "Gly-X-Y". In this amino acid sequence, which is made up of three amino acids, the amino acids other than glycine (namely, X and Y) may each be any of various amino acids.

A collagen molecule has a telopeptide(s) at the amino terminus and/or carboxyl terminus thereof (stated differently, at the amino terminus and/or carboxyl terminus of each polypeptide chain included in the collagen molecule), the telopeptide serving as a main antigen site of collagen. The telopeptide(s) is present in a polypeptide chain in the collagen molecule, outside the above-described triple helical domain and close to the amino terminus or carboxyl terminus.

Treating collagen with an enzyme such as a protease to partially remove telopeptides from the collagen molecules is known to reduce the antigenicity of the collagen molecules to a low level. Such a collagen molecule with a telopeptide(s) partially removed is called an atelocollagen.

Research has so far revealed that collagen, atelocollagen, and a product of degradation of collagen or atelocollagen with a protease each have various physiological functions. There have been developed various uses of collagen, atelocollagen, and a product of degradation of collagen or atelocollagen with a protease on the basis of their physiological functions (see, for example, Patent Literatures 1 and 2).

Patent Literature 1 discloses a technique that allows a degradation product resulting from treating collagen or atelocollagen with a protease (for example, pepsin or actinidain) to be used as a hemostatic medical material. Further specifically, Patent Literature 1 discloses a technique of first treating a skin of a yellowfin tuna with pepsin to obtain an aqueous solution containing atelocollagen and then adding sodium chloride to that aqueous solution to precipitate and recover the atelocollagen. When the atelocollagen is recovered as a precipitate, the sodium chloride is removed together with the supernatant. The technique of Patent Literature 1 next degrades the atelocollagen, recovered as a precipitate, with actinidain to produce a degradation product, so that the degradation product is used as a hemostatic medical material.

Patent Literature 2 discloses a technique that allows a degradation product resulting from treating collagen or atelocollagen with a protease to be used as a composition for prevention or therapy of arteriosclerosis and diseases attributed to arteriosclerosis. Further specifically, Patent Literature 2 discloses a technique that allows a degradation product of collagen which degradation product results from degrading, with a protease, collagen with minerals removed therefrom to be used as a composition for prevention or therapy of arteriosclerosis and diseases attributed to arteriosclerosis.

In a case where collagen or atelocollagen is degraded with a protease as described above, such collagen or atelocollagen is typically degraded under a condition of a low salt concentration. In the case where collagen or atelocollagen has been degraded under such a condition of a low salt concentration, amino acid sequences of the degraded collagen and atelocollagen have already been identified, which are disclosed in, for example, Non Patent Literature 1.

CITATION LIST

Patent Literature

[Patent Literature 1]
  WO 2004/020470 (Publication Date: Mar. 11, 2004)
[Patent Literature 2]
  Japanese Patent Application Publication, Tokukai, No. 2001-31586 A (Publication Date: Feb. 6, 2001)

Non Patent Literature

[Non Patent Literature 1]
  S. Kunii et al., Journal of Biological Chemistry, Vol. 285, No. 23, pp. 17465-17470, Jun. 4, 2010
[Non Patent Literature 2]
  K. Morimoto et al., Bioscience, Biotechnology, and Biochemistry, Vol. 68, pp. 861-867, 2004

SUMMARY OF INVENTION

Technical Problem

While there is ongoing research for physiological functions of collagen, atelocollagen, and a degradation product of collagen or atelocollagen as described above, not all the physiological functions thereof have been elucidated yet.

Discovering new physiological functions of collagen, atelocollagen, and a degradation product of collagen or atelocollagen will contribute greatly to development in various fields such as medical care, food, cosmetics, and basic research.

The present invention has been accomplished in view of the above problem with known techniques. It is an object of the present invention to provide a differentiation-inducing composition containing a degradation product of collagen or atelocollagen.

Solution to Problem

The inventors of the present invention have conducted diligent research in view of the above problem, and have consequently discovered that a degradation product of collagen or atelocollagen which degradation product has a particular structure has the ability to induce cell differentiation. The inventors have thereby completed the present invention.

In order to solve the above problem, a differentiation-inducing composition of the present invention is a differentiation-inducing composition for inducing cell differentiation, the differentiation-inducing composition including: a degradation product of a collagen or an atelocollagen, the degradation product containing at least a portion of a triple helical domain of the collagen or the atelocollagen.

Advantageous Effects of Invention

The present invention produces the effect of inducing cell differentiation.

The present invention produces the effect of inducing differentiation of various kinds of cells.

The present invention produces the effect of inducing cell differentiation rapidly.

The present invention produces the effect of maintaining cell differentiation.

BRIEF DESCRIPTION OF DRAWINGS (a) of FIG. 1 shows a photomicrograph of a spheroid of a mouse preosteoblast cell strain MC3T3-E1 subclone 4, which was induced by a degradation product of an Example of the present invention, whereas (b) of FIG. 1 shows a photomicrograph of a mouse preosteoblast cell strain MC3T3-E1 subclone 4, which is induced by atelocollagen.

Figure 21:
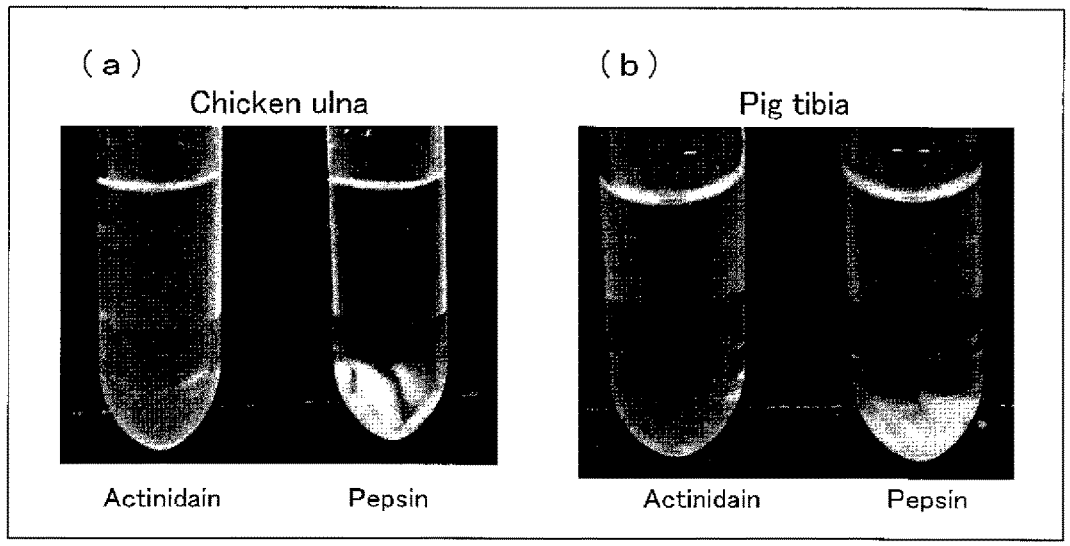

(a) and (b) of FIG. 21 each show a photograph of a bone fragment which was caused to be in contact with enzymes and left to stand for 11 days in an Example of the present invention.

Figure 22:
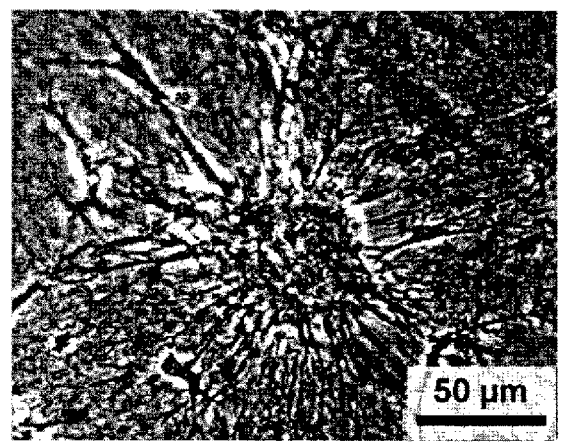

FIG. 22 shows a photograph of a spheroid of human bone marrow mesenchymal stem cells MSC as a result of induction by a bone fragment degradation product in an Example of the present invention.

DESCRIPTION OF EMBODIMENTS

The following description will discuss an embodiment of the present invention. The present invention is, however, not limited to the embodiment below. The present invention is not limited by the description below of any element, but may be variously altered by a skilled person within the scope of the claims. Any embodiment and Example based on a proper combination of technical means disclosed in different embodiments and Examples is also encompassed in the technical scope of the present invention.

Any numerical range "A to B" expressed in the present specification intends to mean not less than A and not more than B.

[1. Differentiation-Inducing Composition]

A differentiation-inducing composition of the present embodiment is a composition for inducing cell differentiation, the differentiation-inducing composition containing a degradation product of collagen or atelocollagen as a main component, the degradation product containing at least a portion of a triple helical domain of the collagen or the atelocollagen. The degradation product may, in other words, contain the entire triple helical domain of collagen or atelocollagen or a portion of the triple helical domain.

Further specifically, the differentiation-inducing composition of the present embodiment is a differentiation-inducing composition containing a degradation product of collagen or atelocollagen, wherein the degradation product results from cleavage of a chemical bond between $X_1$ and $X_2$, between $X_2$ and G, between G and $X_3$, between $X_4$ and G, or between $X_6$ and G in an amino acid sequence in (1) below within the triple helical domain, cleavage of a chemical bond between $X_1$ and $X_2$, between $X_2$ and G, between G and $X_3$, between $X_4$ and G, between $X_6$ and G, between G and $X_7$, or between $X_{14}$ and G in an amino acid sequence in (2) below within triple helical domain, or cleavage of a chemical bond between $Y_1$ and $Y_2$ in an amino acid sequence in (3) below at an amino terminus of the triple helical domain.

The differentiation-inducing composition of the present embodiment may be a differentiation-inducing composition containing a degradation product of collagen or atelocollagen, wherein the degradation product results from cleavage of any one chemical bond selected from a chemical bond between $X_1$ and $X_2$, a chemical bond between $X_2$ and G, a chemical bond between G and $X_3$, a chemical bond between $X_4$ and G, and a chemical bond between $X_6$ and G in an amino acid sequence in (1) below within the triple helical domain, cleavage of a chemical bond selected from any one chemical bond between $X_1$ and $X_2$, a chemical bond between $X_2$ and G, a chemical bond between G and $X_3$, a chemical bond between $X_4$ and G, a chemical bond between $X_6$ and G, a chemical bond between G and $X_7$, and a chemical bond between $X_{14}$ and G in an amino acid sequence in (2) below within the triple helical domain, or cleavage of a chemical bond between $Y_1$ and $Y_2$ in an amino acid sequence in (3) below at an amino terminus of the triple helical domain.

(1) -G-$X_1$-$X_2$-G-$X_3$-$X_4$-G-$X_5$-$X_6$-G- (SEQ ID NO: 1), (2) -G-$X_1$-$X_2$-G-$X_3$-$X_4$-G-$X_5$-$X_6$-G-$X_7$-$X_8$-G-$X_9$-$X_{10}$-G-$X_{11}$-$X_{12}$-G-$X_{13}$-$X_{14}$-G- (SEQ ID NO: 14), (3) -$Y_1$-$Y_2$-$Y_3$-G-$Y_4$-$Y_5$-G-$Y_6$-$Y_7$-G-$Y_8$-$Y_9$-G- (SEQ ID NO: 13), where G represents glycine, and $X_1$ to $X_{14}$ and $Y_1$ to $Y_9$ are each any amino acid.

The following description will discuss the individual elements in detail.

A differentiation-inducing composition of the present embodiment contains a degradation product of collagen or of atelocollagen as a main component.

The collagen or atelocollagen as a material of the degradation product is not limited to any particular one, and may be any well-known collagen or atelocollagen.

Examples of the collagen as a material of the degradation product include collagens of (i) mammals (for example, a cow, a pig, a rabbit, a human, a rat, and a mouse), (ii) birds (for example, a chicken), or (iii) fishes (for example, a shark, a carp, an eel, a tuna [for example, a yellowfin tuna], a tilapia, a sea bream, and a salmon).

Further specifically, examples of the collagen as a material of the degradation product include (i) collagen derived from, for example, a dermis, a tendon, a bone, or a fascia of any of the above mammals or the above birds and (ii) collagen derived from, for example, a skin or a scale of any of the above fishes.

Examples of the atelocollagen as a material of the degradation product include atelocollagen which is produced by treating collagen of any of the above mammals, the above birds, or the above fishes with a protease (for example, pepsin) and in which a telopeptide(s) has been partially removed from the amino terminus and/or carboxyl terminus of the collagen molecules.

A preferable option among the above examples as a material of the degradation product is collagen or atelocollagen of a chicken, a pig, a human, or a rat. A further preferable option among the above examples as a material of the degradation product is collagen or atelocollagen of a pig or a human.

Using collagen or atelocollagen of a fish as a material for the degradation product makes it possible to prepare a material for the degradation product easily and safely in a large amount. A degradation product of such collagen or atelocollagen is safer to the human beings.

In a case where the material for the degradation product is collagen or atelocollagen of a fish, (i) a preferable option is collagen or atelocollagen of a shark, a carp, an eel, a tuna (for example, a yellowfin tuna), a tilapia, a sea bream, or a salmon, and (ii) a further preferable option is collagen or atelocollagen of a tuna, a tilapia, a sea bream, or a salmon.

In a case where the material for the degradation product is atelocollagen, that atelocollagen has a heat denaturation temperature of preferably not lower than 15° C., more preferably not lower than 20° C. In a case where, for example, the material for the degradation product is atelocollagen of a fish, that atelocollagen is preferably atelocollagen of a tuna (for example, a yellowfin tuna), a carp, or the like because such atelocollagen has a heat denaturation temperature of not lower than 25° C.

The above arrangement allows the differentiation-inducing composition of the present embodiment to have a denaturation temperature adjusted preferably to not lower than 15° C., more preferably to not lower than 20° C. The above arrangement consequently allows for production of a differentiation-inducing composition that is excellent in stability in storage and use.

The collagen or atelocollagen as a material of the degradation product may be prepared by a well-known method. For example, collagen-rich tissue of a mammal, a bird, or a fish is put into an acid solution with a pH of approximately 2 to 4 for elution of collagen. Further, a protease such as pepsin is added to the eluate for partial removal of a telopeptide(s) at the amino terminus and/or carboxyl terminus of the collagen molecules, and then a salt such as sodium chloride is added to the eluate to precipitate atelocollagen.

The differentiation-inducing composition of the present embodiment contains:

a degradation product of collagen or atelocollagen which degradation product results from cleavage of a chemical bond between $X_1$ and $X_2$, between $X_2$ and G, between G and $X_3$, between $X_4$ and G, or between $X_6$ and G in the amino acid sequence in (1) below within the triple helical domain of the above collagen or atelocollagen, a degradation product of collagen or atelocollagen which degradation product results from cleavage of a chemical bond between $X_1$ and $X_2$, between $X_2$ and G, between G and $X_3$, between $X_4$ and G, between $X_6$ and G, between G and $X_7$, or between $X_{14}$ and G in the amino acid sequence in (2) below within the triple helical domain of the above collagen or atelocollagen, or a degradation product of collagen or atelocollagen which degradation product results from cleavage of a chemical bond between $Y_1$ and $Y_2$ in the amino acid sequence in (3) below at the amino terminus of the triple helical domain of the above collagen or atelocollagen, (1) -G-$X_1$-$X_2$-G-$X_3$-$X_4$-G-$X_5$-$X_6$-G- (SEQ ID NO:1),
(2) -G-$X_1$-$X_2$-G-$X_3$-$X_4$-G-$X_5$- $X_6$-G-$X_7$-$X_8$-G-$X_9$- $X_{10}$-G-$X_{11}$-$X_{12}$-G-$X_{13}$-$X_{14}$-G- (SEQ ID NO:14),
(3) -$Y_1$-$Y_2$-$Y_3$-G-$Y_4$-$Y_5$-G-$Y_6$- $Y_7$-G-$Y_8$-$Y_9$-G-(SEQ ID NO:13), where G represents glycine, and $X_1$ to $X_{14}$ and $Y_1$ to $Y_9$ are each any amino acid.

The term "triple helical domain" as used in the present specification intends to mean a domain that (i) contains not fewer than 3, preferably not fewer than 80, more preferably not fewer than 300, units of amino acid sequences in tandem each of which units is represented as "Gly-X-Y" (where X and Y each represent an amino acid) and that (ii) contributes to formation of a helical structure.

The cleavage of a chemical bond within the triple helical domain may occur in any of a plurality of kinds of polypeptide chains included in the collagen or atelocollagen.

The cleavage of a chemical bond may occur in, for example, any of the following polypeptide chains: the α 1 chain, the α 2 chain, and the α 3 chain.

The cleavage of a chemical bond occurs preferably in at least one of the α 1 chain and the α 2 chain among the above polypeptide chains.

The cleavage of a chemical bond occurs further preferably in the α 1 chain among the above polypeptide chains.

Preparing a degradation product of collagen or atelocollagen through an enzymatic treatment makes it possible to easily cleave a chemical bond in only a particular polypeptide chain.

The degradation product of collagen or atelocollagen may contain three polypeptide chains in a helical structure. The degradation product of collagen or atelocollagen may alternatively contain three polypeptide chains that are not in a helical structure entirely or partially. Whether the three polypeptide chains are in a helical structure can be determined by a publicly known method (for example, by observing a circular dichroism spectrum of the degradation product).

The degradation product of collagen or atelocollagen basically contains three polypeptide chains. The cleavage of a chemical bond may occur in one, two, or all of the three polypeptide chains.

In a case where the degradation product of collagen or atelocollagen contains three polypeptide chains in a helical structure, a plurality of helical structures may form a meshwork assembly or filamentous assembly.

The term "meshwork" as used in the present specification intends to describe a structure of molecules connected to one another through, for example, hydrogen bonding, electrostatic interaction, or van der Waals bonding to form a three-dimensional mesh and openings therein. The term "filamentous" as used in the present specification intends to describe a substantially linear structure of molecules connected to one another through, for example, hydrogen bonding, electrostatic interaction, or van der Waals bonding. The term "assembly" as used in the present specification intends to mean a structural unit of two or more molecules of an identical kind that bond to one another not through covalent bonding but through interaction with one another. Whether a meshwork or filamentous assembly is present can be determined by observing the degradation product under an electron microscope.

The degradation product of collagen or atelocollagen may have a crosslinked structure. The degradation product may contain, for example, (i) polypeptide chains crosslinked to each other with use of a crosslinking agent, (ii) helical structures crosslinked to each other with use of a crosslinking agent, or (iii) a polypeptide chain and a helical structure crosslinked to each other with use of a crosslinking agent.

The crosslinked structure can be formed by a well-known crosslinking method. Examples of the method include (i) a chemical crosslinking method, (ii) a thermal crosslinking method, and (iii) a crosslinking method involving irradiation with radioactive rays such as ultraviolet rays.

The chemical crosslinking involves use of, for example, a crosslinking agent such as (i) a water-soluble carbodiimide compound such as 1-ethyl-3-(3-dimethylaminopropyl)carbodiimide hydrochloride, (ii) epichlorohydrin, (iii) a diepoxy compound such as bisepoxy diethylene glycol, or (iv) $NaBH_4$.

The crosslinking agent has a concentration of preferably $10^{-3}$ mass % to 10 mass % with respect to the degradation product of collagen or atelocollagen. The crosslinked structure can be formed by preferably causing the degradation product of collagen or atelocollagen to contact with a crosslinking agent at a temperature of 5° C. to 40° C. for 3 hours to 48 hours In a case where the degradation product of collagen or atelocollagen is to be irradiated with ultraviolet rays for a crosslinking process, the degradation product is, for example, irradiated with ultraviolet rays at room temperature for approximately 3 hours to 48 hours with use of an ultraviolet lamp or the like for formation of a crosslinked structure.

In a case where the degradation product of collagen or atelocollagen is to be thermally crosslinked, the degradation product is heated under reduced pressure at a temperature of preferably approximately 110° C. to 160° C. for approximately 3 hours to 48 hours to for formation of a crosslinked structure.

The degradation product of collagen or atelocollagen, in a case where it has a crosslinked structure, advantageously has an improved collagenase resistance property and an increased strength.

The degradation product of collagen or atelocollagen may as necessary have a desired chemical modification. Example kinds of the chemical modification include acylation, myristylation, and polyethyleneglycol modification.

For example, the degradation product of collagen or atelocollagen can be subjected to succinylation (which is a kind of acylation) by causing the degradation product to react with succinic anhydride in a solvent having a neutral pH such as a phosphate buffer. Succinylation can improve the solubility of the degradation product in a solvent having a neutral pH.

The degradation product of collagen or atelocollagen can be subjected to polyethyleneglycol modification by causing the degradation product to react with polyethyleneglycol activated with cyanuric chloride.

The above-described degradation product of collagen or atelocollagen results from cleavage of a chemical bond between $X_1$ and $X_2$, between $X_2$ and G, between G and $X_3$, between $X_4$ and G, or between $X_6$ and G in an amino acid sequence in (1) below within the above-described triple helical domain, (1)-G-$X_1$-$X_2$-G-$X_3$- $X_4$-G-$X_5$-$X_6$-G-(SEQ ID NO:1),
where G represents glycine, and $X_1$ to $X_6$ each represent any amino acid.

The above-described degradation product of collagen or atelocollagen results from cleavage of a chemical bond between $X_1$ and $X_2$, between $X_2$ and G, between G and $X_3$, between $X_4$ and G, between $X_6$ and G, between G and $X_7$, or between $X_{14}$ and G in an amino acid sequence in (2) below within the above-described triple helical domain, (2)-G-$X_1$-$X_2$-G-$X_3$-$X_4$-G-$X_5$-$X_6$-G-$X_7$-$X_8$-G-$X_9$-$X_{10}$-G-$X_{11}$-$X_{12}$-G-$X_{13}$$X_{14}$-G- (SEQ ID NO:14), where G represents glycine, and $X_1$ to $X_{14}$ each represent any amino acid.

The above-described degradation product of collagen or atelocollagen results from cleavage of a chemical bond between $Y_1$ and $Y_2$ in an amino acid sequence in (3) below at the amino terminus of the above-described triple helical domain, (3)-$Y_1$-$Y_2$-$Y_3$- G-$Y_4$-$Y_5$- G-$Y_6$-$Y_7$- G-$Y_8$-$Y_9$-G-(SEQ ID NO:13), where G represents glycine, and $Y_1$ to $Y_9$ each represent any amino acid.

The amino acid sequence in (1) or (2) above may be at any position within the triple helical domain. The amino acid sequence in (1) or (2) above may be, for example, at a position away from the two terminuses of the triple helical domain, but is preferably at the amino terminus of the triple helical domain. Stated differently, that "G" in the amino acid sequence in (1) or (2) above which is closest to the amino terminus preferably corresponds to that "G" within the triple helical domain which is closest to the amino terminus.

In a case where the amino acid sequence in (1) or (2) above is at a position away from the two terminuses of the triple helical domain, the amino acid sequence in (1) or (2) may be at any specific position. The amino acid sequence in (1) or (2) may be connected, at the amino terminus of the amino acid sequence in (1) or (2), to not fewer than 1, not fewer than 5, not fewer than 10, not fewer than 50, not fewer than 100, not fewer than 150, not fewer than 200, not fewer than 250, or not fewer than 300, units of amino acid sequences in tandem each of which units is represented as "Gly-X-Y" (where X and Y each represent an amino acid). The amino acid sequence in (1) or (2) may be connected, at the carboxyl terminus of the amino acid sequence in (1) or (2), to not fewer than 1, not fewer than 5, not fewer than 10, not fewer than 50, not fewer than 100, not fewer than 150, not fewer than 200, not fewer than 250, or not fewer than 300, units of amino acid sequences in tandem each of which units is represented as "Gly-X-Y" (where X and Y each represent an amino acid).

$X_1$ to $X_6$ can each be any amino acid, and are each not limited to any particular kind. At least two of $X_1$ to $X_6$ may be amino acids of an identical kind. $X_1$ to $X_6$ may alternatively be amino acids all of which differ from one another in kind.

$X_1$ to $X_6$ may each be, for example, any of the following amino acids: glycine, alanine, valine, leucine, isoleucine, serine, threonine, tyrosine, cysteine, methionine, aspartic acid, asparagine, glutamic acid, glutamine, arginine, lysine, histidine, phenylalanine, tyrosine, tryptophan, hydroxyproline, and hydroxylysine.

Further specifically, $X_1$ to $X_6$ may be such that $X_1$, $X_3$, and $X_5$ are an identical amino acid, while the others are different amino acids.

Further specifically, $X_1$ to $X_6$ may be such that at least one selected from the group consisting of $X_1$, $X_3$, and $X_5$ is proline, while the others are each any amino acid.

Further specifically, $X_1$ to $X_6$ may be such that $X_1$ is proline, while $X_2$ to $X_6$ are each any amino acid.

Further specifically, $X_1$ to $X_6$ may be such that $X_1$ and $X_3$ are each proline, while $X_2$ and $X_4$ to $X_6$ are each any amino acid.

Further specifically, $X_1$ to $X_6$ may be such that $X_1$, $X_3$, and $X_5$ are each proline, while $X_2$, $X_4$, and $X_6$ are each any amino acid.

Further specifically, $X_1$ to $X_6$ may be such that (i) $X_1$, $X_3$, and $X_5$ are each proline, (ii) $X_2$ is an amino acid containing a sulfur atom in a side chain (for example, cysteine or methionine) or an amino acid containing a hydroxyl group in a side chain (for example, hydroxyproline, hydroxylysine, or serine), and (iii) $X_4$ and $X_6$ are each any amino acid.

Further specifically, $X_1$ to $X_6$ may be such that (i) $X_1$, $X_3$, and $X_5$ are each proline, (ii) $X_2$ is an amino acid containing a sulfur atom in a side chain (for example, cysteine or methionine), (iii) $X_4$ is an amino acid having an aliphatic side chain (for example, glycine, alanine, valine, leucine, or isoleucine) or an amino acid containing a hydroxyl group in a side chain (for example, hydroxyproline, hydroxylysine, or serine), and (iv) $X_6$ is any amino acid.

Further specifically, $X_1$ to $X_6$ may be such that $X_1$, $X_3$, and $X_5$ are each proline, (ii) $X_2$ is an amino acid containing a sulfur atom in a side chain (for example, cysteine or methionine), (iii) $X_4$ is an amino acid having an aliphatic side chain (for example, glycine, alanine, valine, leucine, or isoleucine) or an amino acid containing a hydroxyl group in a side chain (for example, hydroxyproline, hydroxylysine, or serine), and (iv) $X_6$ is an amino acid containing a base in a side chain (for example, arginine, lysine, or histidine).

Further specifically, $X_1$ to $X_6$ may be such that (i) $X_1$, $X_3$, and $X_5$ are each proline, (ii) $X_2$ is methionine, (iii) $X_4$ is alanine or serine, and (iv) $X_6$ is arginine.

In the amino acid sequence in (2) above, $X_1$ to $X_6$ may be identical in arrangement to the above $X_1$ to $X_6$, respectively. The following description will discuss detailed arrangements of $X_7$ to $X_{14}$.

$X_7$ to $X_{14}$ can each be any amino acid, and are each not limited to any particular kind. At least two of $X_7$ to $X_{14}$ may be amino acids of an identical kind. $X_7$ to $X_{14}$ may alternatively be amino acids all of which differ from one another in kind.

$X_7$ to $X_{14}$ may each be, for example, any of the following amino acids: glycine, alanine, valine, leucine, isoleucine, serine, threonine, tyrosine, cysteine, methionine, aspartic acid, asparagine, glutamic acid, glutamine, arginine, lysine, histidine, phenylalanine, tyrosine, tryptophan, hydroxyproline, and hydroxylysine.

Further specifically, $X_7$ to $X_{14}$ may be such that $X_8$, $X_9$, $X_{10}$, $X_{12}$, and $X_{13}$ are an identical amino acid, while the others are different amino acids.

Further specifically, $X_7$ to $X_{14}$ may be such that at least one selected from the group consisting of $X_8$, $X_9$, $X_{10}$, $X_{12}$, and $X_{13}$ is proline or hydroxyproline, while the others are each any amino acid.

Further specifically, $X_7$ to $X_{14}$ may be such that $X_8$ is proline or hydroxyproline, while the others are each any amino acid.

Further specifically, $X_7$ to $X_{14}$ may be such that $X_8$ and $X_9$ are each proline or hydroxyproline, while the others are each any amino acid.

Further specifically, $X_7$ to $X_{14}$ may be such that $X_8$, $X_9$, and $X_{10}$ are each proline or hydroxyproline, while the others are each any amino acid.

Further specifically, $X_7$ to $X_{14}$ may be such that $X_8$, $X_9$, $X_{10}$, and $X_{12}$ are each proline or hydroxyproline, while the others are each any amino acid.

Further specifically, $X_7$ to $X_{14}$ may be such that $X_8$, $X_9$, $X_{10}$, $X_{12}$, and $X_{13}$ are each proline or hydroxyproline, while the others are each any amino acid.

Further specifically, $X_7$ to $X_{14}$ may be such that (i) $X_8$, $X_9$, $X_{10}$, $X_{12}$, and $X_{13}$ are each proline or hydroxyproline, (ii) $X_7$ is an amino acid having an aliphatic side chain (for example, glycine, alanine, valine, leucine, or isoleucine), and (iii) the others are each any amino acid.

Further specifically, $X_7$ to $X_{14}$ may be such that (i) $X_8$, $X_9$, $X_{10}$, $X_{12}$, and $X_{13}$ are each proline or hydroxyproline, (ii) $X_7$ and $X_{11}$ are each an amino acid having an aliphatic side chain (for example, glycine, alanine, valine, leucine, or isoleucine), and (iii) the rest is any amino acid.

Further specifically, $X_7$ to $X_{14}$ may be such that (i) $X_8$, $X_9$, $X_{10}$, $X_{12}$, and $X_{13}$ are each proline or hydroxyproline, (ii) $X_7$ and $X_{11}$ are each an amino acid having an aliphatic side chain (for example, glycine, alanine, valine, leucine, or isoleucine), and (iii) $X_{14}$ is an amino acid having a hydrophilic and non-dissociative side chain (serine, threonine, asparagine, or glutamine).

Further specifically, $X_7$ to $X_{14}$ may be such that (i) $X_8$, $X_9$, $X_{10}$, $X_{12}$, and $X_{13}$ are each proline or hydroxyproline, (ii) $X_7$ is leucine, (iii) $X_{11}$ is alanine, and (iv) $X_{14}$ is glutamine.

The amino acid sequence in (3) above is positioned at the amino terminus of the triple helical domain. This means that (i) G between $Y_3$ and $Y_4$ indicates that glycine within the triple helical domain which is closest to the amino terminus and that (ii) $Y_1$, $Y_2$, and $Y_3$ indicate those amino acids in a plurality of kinds of polypeptide chains included in the collagen or atelocollagen which are positioned outside the triple helical domain and close to the amino terminus of the triple helical domain.

$Y_1$ to $Y_9$ can each be any amino acid, and are each not limited to any particular kind. At least two of $Y_1$ to $Y_9$ may be amino acids of an identical kind. $Y_1$ to $Y_9$ may alternatively be amino acids all of which differ from one another in kind.

$Y_1$ to $Y_9$ may each be, for example, any of the following amino acids: glycine, alanine, valine, leucine, isoleucine, serine, threonine, tyrosine, cysteine, methionine, aspartic acid, asparagine, glutamic acid, glutamine, arginine, lysine, histidine, phenylalanine, tyrosine, tryptophan, hydroxyproline, and hydroxylysine.

Further specifically, $Y_1$ to $Y_3$ may be such that $Y_3$ is proline, while $Y_1$ and $Y_2$ are each any amino acid.

Further specifically, $Y_1$ to $Y_3$ may be such that $Y_3$ is proline, while $Y_1$ and $Y_2$ are each an amino acid having an aliphatic side chain (for example, glycine, alanine, valine, leucine, or isoleucine) or an amino acid containing a hydroxyl group in a side chain (hydroxyproline, hydroxylysine, or serine).

Further specifically, $Y_1$ to $Y_3$ may be such that (i) $Y_3$ is proline, (ii) $Y_1$ is alanine or serine, and (iii) $Y_2$ is valine.

In any of the above cases, $Y_4$ to $Y_9$ are not particularly limited in terms of specific arrangements. $Y_4$ to $Y_9$ may be such that (i) $Y_4$ and $X_1$ are an identical amino acid, (ii) $Y_5$ and $X_2$ are an identical amino acid, (iii) $Y_6$ and $X_3$ are an identical amino acid, (iv) $Y_7$ and $X_4$ are an identical amino acid, (v) $Y_8$ and $X_5$ are an identical amino acid, and (vi) $Y_9$ and $X_6$ are an identical amino acid.

Conventional collagen and atelocollagen are difficult to dissolve at temperatures close to human body temperatures.

The degradation product of collagen or atelocollagen for the present invention can, on the other hand, be in a liquid state at temperatures close to human body temperatures. Thus, the differentiation-inducing composition of the present embodiment is, in a case where it is used for human tissues (for example, bone, fat, cartilage, and nerve) or the like, easily compatible with those tissues.

The degradation product of collagen or atelocollagen for the present invention starts to gelate at a high concentration as compared with conventional degradation products of collagen or atelocollagen. This allows for stable, normal-temperature preservation of a concentration of the degradation product of collagen or atelocollagen for the present invention which concentration is equal to the concentrations at which conventional degradation products of collagen or atelocollagen gelate. This means that the differentiation-inducing composition of the present embodiment can be stably preserved at a normal temperature.

The degradation product of collagen or atelocollagen for the present invention results from cleavage of a chemical bond between $X_1$ and $X_2$, between $X_2$ and G, between G and $X_3$, between $X_4$ and G, or between $X_6$ and G in the amino acid sequence in (1) within the triple helical domain of the collagen or atelocollagen.

The degradation product of collagen or atelocollagen for the present invention results from cleavage of a chemical bond between $X_1$ and $X_2$, between $X_2$ and G, between G and $X_3$, between $X_4$ and G, between $X_6$ and G, between G and $X_7$, or between $X_{14}$ and G in the amino acid sequence in (2) within the triple helical domain of the collagen or atelocollagen.

The degradation product of collagen or atelocollagen for the present invention results from cleavage of a chemical bond between $Y_1$ and $Y_2$ in the amino acid sequence in (3) at the amino terminus of the triple helical domain of the collagen or atelocollagen.

The cleavage can be carried out as appropriate by a desired method.

An example method is a method of chemically synthesizing collagen or atelocollagen having an already cleaved chemical bond. This chemical synthesis can be a typical, well-known method of chemical synthesis.

Alternatively, collagen or atelocollagen having an already cleaved chemical bond may also be prepared as follows: DNA that encodes collagen or atelocollagen having an already cleaved chemical bond is inserted into a well-known protein expression vector. This protein expression vector is then transferred into a desired host (for example, *Escherichia coli*, yeast, insect cell, or animal cell). Next, expression of the collagen or atelocollagen, which has an already cleaved chemical bond, is induced in the host.

Alternatively, the cleavage may be carried out by degrading collagen or atelocollagen with use of an enzyme (for example, a protease such as cysteine protease).

The method for the cleavage will be detailed later.

[2. Method for Producing Differentiation-Inducing Composition Containing Degradation Product of Collagen or Atelocollagen]

A method for producing a differentiation-inducing composition of the present embodiment containing a degradation product of collagen or atelocollagen is a production method including:

(A) a step of cleaving a chemical bond between $X_1$ and $X_2$, between $X_2$ and G, between G and $X_3$, between $X_4$ and G, or between $X_6$ and G in the amino acid sequence in (1) below within the triple helical domain of collagen or atelocollagen, (B) a step of cleaving a chemical bond between $X_1$ and $X_2$, between $X_2$ and G, between G and $X_3$, between $X_4$ and G, between $X_6$ and G, between G and $X_7$, or between $X_{14}$ and G in the amino acid sequence in (2) below within the triple helical domain of collagen or atelocollagen, or (C) a step of cleaving a chemical bond between $Y_1$ and $Y_2$ in the amino acid sequence in (3) below at the amino terminus of the triple helical domain of collagen or atelocollagen.

An alternative method for producing a differentiation-inducing composition of the present embodiment containing a degradation product of collagen or atelocollagen may be a production method including:

(D) a step of cleaving any one chemical bond selected from a chemical bond between $X_1$ and $X_2$, a chemical bond between $X_2$ and G, a chemical bond between G and $X_3$, a chemical bond between $X_4$ and G, and a chemical bond between $X_6$ and G in the amino acid sequence in (1) below within the triple helical domain of collagen or atelocollagen, (E) a step of cleaving any one chemical bond selected from a chemical bond between $X_1$ and $X_2$, a chemical bond between $X_2$ and G, a chemical bond between G and $X_3$, a chemical bond between $X_4$ and G, a chemical bond between $X_6$ and G, a chemical bond between G and $X_7$, and a chemical bond between $X_{14}$ and G in the amino acid sequence in (2) below within the triple helical domain of collagen or atelocollagen, or (F) a step of cleaving a chemical bond between $Y_1$ and $Y_2$ in the amino acid sequence in (3) below at the amino terminus of the triple helical domain of collagen or atelocollagen.

(1) -G-$X_1$-$X_2$-G-$X_3$-$X_4$-G-$X_5$-$X_6$-G-
(2) -G-$X_1$-$X_2$-G-$X_3$-$X_4$-G-$X_5$-$X_6$-G-$X_7$-$X_8$-G-$X_9$-$X_{10}$-G-$X_{11}$-$X_{12}$-G-$X_{13}$- $X_{14}$-G-(SEQ ID NO:14),
(3) -$Y_1$-$Y_2$-$Y_3$-G-$Y_4$-$Y_5$-G-$Y_6$-$Y_7$-G-$Y_8$-$Y_9$-G-(SEQ ID NO:13), where G represents glycine, and $X_1$ to $X_{14}$ and $Y_1$ to $Y_9$ are each any amino acid.

The following description will discuss the individual steps in detail. The degradation product of collagen or atelocollagen for the present invention is described above, and is not described below.

The cleaving step above may be any step of cleaving a chemical bond at a particular position in the amino acid sequences in (1) to (3), and is not particularly limited in terms of specific arrangements.

The cleaving step may be a step of actually cleaving a chemical bond within the triple helical domain to prepare a degradation product of collagen or atelocollagen (for example, an enzyme method).

The cleaving step for the present invention may alternatively cover in concept a step of preparing a degradation product of collagen or atelocollagen which degradation product has an already cleaved chemical bond within the triple helical domain (for example, chemical synthesis and expression of recombinant protein).

The following description will discuss the cleaving step in detail.

[2-1. Cleaving Step Based on Enzyme Method]

In a case where the cleaving step is based on an enzyme method, the cleaving step can, for example, be carried out as described below.

The cleaving step can involve degrading collagen or atelocollagen with use of an enzyme (for example, a protease such as cysteine protease).

The enzyme is not limited to any particular one, and is preferably a cysteine protease, for example.

The cysteine protease is preferably (i) a cysteine protease that contains a larger amount of basic amino acids than the amount of acidic amino acids that it contains or (ii) a cysteine protease that is active at a hydrogen ion concentration in an acidic region.

Examples of such a cysteine protease include cathepsin B [EC 3.4.22.1], papain [EC 3.4.22.2], ficin [EC 3.4.22.3], actinidain [EC 3.4.22.14], cathepsin L [EC 3.4.22.15], cathepsin H [EC 3.4.22.16], cathepsin S [EC 3.4.22.27], bromelain [EC 3.4.22.32], cathepsin K [EC 3.4.22.38], alloline, and calcium dependent protease.

Preferable among the above are papain, ficin, actinidain, cathepsin K, alloline, and bromelain. Further preferable among the above are papain, ficin, actinidain, and cathepsin K.

The enzyme can be prepared by a publicly known method. Examples of such a method include (i) a method of preparing an enzyme by chemical synthesis, (ii) a method of extracting an enzyme from a bacterium, a fungus, or a cell or tissue of any of various animals and plants, and (iii) a method of preparing an enzyme by a genetic engineering means. The enzyme can alternatively be a commercially available enzyme as well.

In a case where the cleaving step involves degrading collagen or atelocollagen with use of an enzyme (for example, a protease), the cleaving step can be carried out by, for example, any of the methods (i) to (iii) below. The methods (i) to (iii) below are, however, mere examples of the cleaving step: The present invention is not limited by the description of the methods (i) to (iii).

The methods (i) and (ii) below are each an example method for cleaving a chemical bond at a particular position in the amino acid sequence in (1) or (2), whereas the method (iii) below is an example method for cleaving a chemical bond at a particular position in the amino acid sequence in (3).

(i) Method of causing collagen or atelocollagen to be in contact with an enzyme in the presence of a salt having a high concentration.

(ii) Method of causing collagen or atelocollagen to be in contact with an enzyme having been in contact with a salt having a high concentration.

(iii) Method of causing collagen or atelocollagen to be in contact with an enzyme in the presence of a salt having a low concentration.

A specific example of the method (i) above is a method of causing collagen or atelocollagen to be in contact with an enzyme in an aqueous solution containing a salt at a high concentration.

A specific example of the method (ii) above is a method of causing an enzyme to be in contact in advance with an aqueous solution containing a salt at a high concentration and then causing collagen or atelocollagen to be in contact with that enzyme.

A specific example of the method (iii) above is a method of causing collagen or atelocollagen to be in contact with an enzyme in an aqueous solution containing a salt at a low concentration.

The aqueous solution is not particularly limited in terms of specific arrangements. The aqueous solution can, for example, contain water as a solvent.

The salt is not particularly limited in terms of specific arrangements, but is preferably a chloride. The chloride is not limited to any particular one. Examples of the chloride include NaCl, KCl, LiCl, and $MgCl_2$.

The salt contained in the aqueous solution at a high concentration may have any concentration. A higher concentration is, however, more preferable. The concentration is, for example, preferably not less than 200 mM, more preferably not less than 500 mM, even more preferably not less than 1000 mM, even more preferably not less than 1500 mM, most preferably not less than 2000 mM.

The concentration of the salt contained in the aqueous solution at a high concentration may have any upper limit. The upper limit may be 2500 mM, for example. A salt concentration of higher than 2500 mM will salt out a large amount of protein, with the result that the enzymatic degradation of collagen or atelocollagen tends to have a decreased efficiency. A salt concentration of not more than 2500 mM allows for a higher efficiency of enzymatic degradation of collagen or atelocollagen.

It follows that the concentration of the salt contained in the aqueous solution at a high concentration is preferably within a range of not less than 200 mM and not more than 2500 mM, more preferably within a range of not less than 500 mM and not more than 2500 mM, even more preferably within a range of not less than 1000 mM and not more than 2500 mM, even more preferably within a range of not less than 1500 mM and not more than 2500 mM, most preferably within a range of not less than 2000 mM and not more than 2500 mM.

A higher concentration of the salt contained in the aqueous solution at a high concentration can increase the specificity of the position of the enzymatic cleavage of a chemical bond in collagen or atelocollagen. This allows the degradation product of collagen or atelocollagen for the present invention to be more uniform and have higher physiological activity.

The salt contained in the aqueous solution at a low concentration may have any concentration. A lower concentration is, however, more preferable. The concentration is, for example, preferably lower than 200 mM, more preferably not more than 150 mM, even more preferably not more than 100 mM, even more preferably not more than 50 mM, most preferably substantially 0 mM.

Collagen or atelocollagen may be dissolved in the aqueous solution (for example, water) in any amount. For example, 1 part by weight of collagen or atelocollagen is preferably dissolved in 1000 parts by weight to 10000 parts by weight of the aqueous solution.

With the above arrangement, in a case where the enzyme has been added to the aqueous solution, the enzyme comes into contact efficiently with the collagen or atelocollagen. This in turn allows the collagen or atelocollagen to be degraded efficiently with use of the enzyme (for example, a protease).

The enzyme may be added to the aqueous solution in any amount. For example, 10 parts by weight to 20 parts by weight of the enzyme is preferably added to 100 parts by weight of the collagen or atelocollagen.

With the above arrangement, the aqueous solution has a high enzyme concentration. This allows the collagen or atelocollagen to be degraded efficiently with use of the enzyme (for example, a protease).

Other conditions (for example, the pH and temperature of the aqueous solution, and the contact period) under which the collagen or atelocollagen is caused to be in contact with the enzyme in the aqueous solution are not particularly limited, and may be set as appropriate. Such other conditions are, however, preferably within the ranges below.

(1) The aqueous solution has a pH of preferably 2.0 to 7.0, further preferably 2.5 to 6.5. The aqueous solution can contain a well-known buffer to have a pH kept within the above range. The aqueous solution having a pH within the above range allows collagen or atelocollagen to be dissolved therein uniformly, and consequently allows an enzymatic reaction to occur efficiently.

(2) The temperature of the aqueous solution is not limited to any particular value, and may be selected in view of the enzyme used. The temperature is, for example, preferably within a range of 15° C. to 40° C., more preferably within a range of 20° C. to 35° C.

(3) The contact period is not limited to any particular length, and may be selected in view of the amount of the enzyme and/or the amount of the collagen or atelocollagen.

The contact period is, for example, preferably within a range of 1 hour to 60 days, more preferably within a range of 1 day to 7 days, further preferably within a range of 3 days to 7 days.

A method for the present embodiment may include, as necessary, at least one step selected from the group consisting of a step of readjusting the pH, a step of inactivating the enzyme, and a step of removing contaminants, after the collagen or atelocollagen is caused to be in contact with the enzyme in the aqueous solution.

The step of removing contaminants can be carried out by a typical method for separating a substance. The step of removing contaminants can be carried out by, for example, dialysis, salting-out, gel filtration chromatography, isoelectric precipitation, ion exchange chromatography, or hydrophobic interaction chromatography.

The cleaving step can be carried out by degrading the collagen or atelocollagen with use of the enzyme as described above. The collagen or atelocollagen to be degraded may be contained in biological tissue. In other words, the cleaving step can be carried out by causing such biological tissue to be in contact with the enzyme.

The biological tissue is not limited to any particular tissue, and can be, for example, a dermis, a tendon, a bone, or a fascia of a mammal or a bird, or a skin or a scale of a fish.

The biological tissue is preferably a bone from the viewpoint of maintaining high physiological activity and the ability to produce a degradation product of collagen or atelocollagen in a large amount.

In a case where the biological tissue is a bone, the bone is preferably caused to be in contact with the enzyme in an acidic condition. The acidic condition is, for example, preferably a pH of 2.5 to 6.5, further preferably a pH of 2.5 to 5.0, even further preferably a pH of 2.5 to 4.0, most preferably a pH of 2.5 to 3.5.

More specifically, a method for the present invention for producing a degradation product of collagen or atelocollagen is preferably arranged such that the cleaving step is a step of causing a bone to be in contact with the cysteine protease for contact of collagen in the bone with the cysteine protease.

The method for the present invention for producing a degradation product of collagen or atelocollagen is preferably arranged such that the cleaving step is a step of causing a bone to be in contact with the cysteine protease in the presence of a salt having a concentration of not less than 200 mM.

The method for the present invention for producing a degradation product of collagen or atelocollagen is preferably arranged such that the cleaving step is a step of causing a bone to be in contact with a cysteine protease having been in contact with a salt having a concentration of not less than 200 mM.

The method for the present invention for producing a degradation product of collagen or atelocollagen is preferably arranged such that the cleaving step is a step of causing a bone to be in contact with the cysteine protease in the presence of a salt having a concentration lower than 200 mM.

[2-2. Chemical Synthesis]

In a case where the cleaving step is based on chemical synthesis, the cleaving step can be arranged as below, for example.

First, information on the respective amino acid sequences of polypeptide chains included in collagen or atelocollagen is obtained from a well-known database. The polypeptide chains may be selected as appropriate in accordance with the type of collagen or atelocollagen. The information may be on the amino acid sequence of a single kind of polypeptide chain or on the respective polypeptide chains of a plurality of kinds of polypeptide chains.

Next, a polypeptide chain having a chemical bond to be cleaved is selected from the above polypeptide, and the position of such a chemical bond to be cleaved is selected. Further, the amino acid sequence of a desired polypeptide chain after cleavage of the chemical bond is determined.

Finally, the desired polypeptide chain is synthesized by a well-known chemical synthesis method in accordance with the amino acid sequence determined.

The cleaving step can be carried out as described above.

A method for producing the differentiation-inducing composition of the present embodiment may include a step other than the cleaving step described above.

For example, a method for producing the differentiation-inducing composition of the present embodiment may include a step of, after the desired polypeptide chain is synthesized by a well-known chemical synthesis method, purifying the synthesized polypeptide chain. The purification may be carried out with use of a well-known column as appropriate.

A method for producing the differentiation-inducing composition of the present embodiment may include a step of mixing the desired polypeptide chain with another polypeptide chain. Such another polypeptide chain is not limited to any particular polypeptide chain, and may be a polypeptide chain similarly having a cleaved chemical bond or a polypeptide chain having no cleaved chemical bond.

[2-3. Cleaving Step Based on Expression of Recombinant Protein]

In a case where the cleaving step is based on expression of recombinant protein, the cleaving step can be arranged as below, for example.

First, information on the respective amino acid sequences of polypeptide chains included in collagen or atelocollagen is obtained from a well-known database. The polypeptide chains may be selected as appropriate in accordance with the type of collagen or atelocollagen. The information may be on the amino acid sequence of a single kind of polypeptide chain or on the respective polypeptide chains of a plurality of kinds of polypeptide chains.

Next, a polypeptide chain having a chemical bond to be cleaved is selected from the above polypeptide, and the position of such a chemical bond to be cleaved is selected. Further, the amino acid sequence and DNA sequence of a desired polypeptide chain after cleavage of the chemical bond is determined.

Next, DNA that encodes the desired polypeptide chain is inserted into a well-known protein expression vector. This protein expression vector is then transferred into a desired host (for example, *Escherichia coli*, yeast, insect cell, or animal cell). After that, a polypeptide chain having a cleaved chemical bond is expressed in the host.

The cleaving step can be carried out as described above.

A method for producing the differentiation-inducing composition of the present embodiment may include a step other than the cleaving step described above.

For example, a method for producing the differentiation-inducing composition of the present embodiment may include a step of, after the desired polypeptide chain is expressed in the host, purifying the expressed polypeptide chain. The purification may be carried out with use of a well-known column as appropriate.

A method for producing the differentiation-inducing composition of the present embodiment may include a step of mixing the desired polypeptide chain with another polypeptide chain. Such another polypeptide chain is not limited to any particular polypeptide chain, and may be a polypeptide chain similarly having a cleaved chemical bond or a polypeptide chain having no cleaved chemical bond.

[3. Use of Differentiation-Inducing Composition]

The differentiation-inducing composition of the present embodiment functions to induce cell differentiation.

Further specifically, the differentiation-inducing composition of the present embodiment functions to induce cells to differentiate into a bone (specifically, a osteoblast), fat, cartilage, nerve, or the like.

The differentiation-inducing composition of the present embodiment contains a degradation product of collagen or atelocollagen as a main component having differentiation-inducing activity.

The differentiation-inducing composition of the present embodiment may contain a degradation product of collagen or atelocollagen in any amount. A larger amount of a degradation product of collagen or atelocollagen leads to a greater differentiation-inducing effect, and is thus preferable.

For example, the differentiation-inducing composition of the present embodiment may contain a degradation product of collagen or atelocollagen in an amount within a range of 0.1 weight % to 100 weight %. The amount is, however, preferably within a range of 50 weight % to 100 weight %, more preferably within a range of 90 weight % to 100 weight %, most preferably 100 weight %.

The differentiation-inducing composition of the present embodiment may further contain components other than the degradation product of collagen or atelocollagen. Such components are not limited to any particular ones. The differentiation-inducing composition may contain a desired component(s) as appropriate.

The present invention may alternatively be arranged as described below.

<1> In order to solve the above problem, a differentiation-inducing composition of the present invention is a differentiation-inducing composition for inducing cell differentiation, the differentiation-inducing composition including: a degradation product of a collagen or an atelocollagen, the degradation product containing at least a portion of a triple helical domain of the collagen or the atelocollagen.

<2> A differentiation-inducing composition of the present invention is preferably a differentiation-inducing composition, wherein the degradation product results from cleavage of a chemical bond between $X_1$ and $X_2$, between $X_2$ and G, between G and $X_3$, between $X_4$ and G, or between $X_6$ and G in an amino acid sequence in (1) below within the triple helical domain, cleavage of a chemical bond between $X_1$ and $X_2$, between $X_2$ and G, between G and $X_3$, between $X_4$ and G, between $X_6$ and G, between G and $X_7$, or between $X_{14}$ and G in an amino acid sequence in (2) below within triple helical domain, or cleavage of a chemical bond between $Y_1$ and $Y_2$ in an amino acid sequence in (3) below at an amino terminus of the triple helical domain, (1) -G-$X_1$-$X_2$-G-$X_3$- $X_4$-G-$X_5$- $X_6$-G-

(2) -G-$X_1$-$X_2$-G-$X_3$-$X_4$-G-$X_5$-$X_6$-G-$X_7$-$X_8$-G-$X_9$-$X_{10}$-G-$X_{11}$-$X_{12}$-G-$X_{13}$- $X_{14}$-G-(SEQ ID NO:14), (3) -$Y_1$-$Y_2$-$Y_3$-G-$Y_4$-$Y_5$-G-$Y_6$-$Y_7$-G-$Y_8$-$Y_9$-G-(SEQ ID NO:13), (3) -$Y_1$-$Y_2$-$Y_3$-G-$Y_4$-$Y_5$-G-$Y_6$-$Y_7$-G-$Y_8$-$Y_9$-G-(SEQ ID NO:13), where G represents glycine, and $X_1$ to $X_{14}$ and $Y_1$ to $Y_9$ each represent an amino acid.

<3> A differentiation-inducing composition of the present invention is preferably a differentiation-inducing composition, wherein the amino acid sequence in (1) or (2) is at an amino terminus of the triple helical domain.

<4> A differentiation-inducing composition of the present invention is preferably a differentiation-inducing composition, wherein the cleavage in the amino acid sequence in (1), (2), or (3) is within at least one of an α 1 chain and an α 2 chain of the collagen or the atelocollagen.

EXAMPLES

<1. Influence of Salt Concentration on Cleavage in Pig-Derived α 1 Chain>

First, 50 mM citric acid buffer solutions (pH of 3.0) each containing sodium chloride at a concentration of 0 mM, 200 mM, 1000 mM, 1500 mM, or 2000 mM was prepared. Water was used as a solvent of these aqueous solutions.

For activation of actinidain, actinidain was dissolved in a 50 mM phosphate buffer (pH of 6.5) containing 10 mM dithiothreitol, and a resultant aqueous solution was left to stand at 25° C. for 90 minutes. Note that actinidain had been purified by a well-known method (see, for example, Non Patent Literature 2).

Next, pig-derived type I collagen was dissolved in the 50 mM citric acid buffer solutions (pH of 3.0) containing the salt. Resultant solutions containing pig-derived type I collagen were caused to be in contact with the aqueous solution containing actinidain at 20° C. for not shorter than 10 days to prepare degradation products of type I collagen. Note that pig-derived type I collagen had been purified by a well-known method (see, for example, Non Patent Literature 2).

The degradation products of type I collagen thus prepared were separated by polyacrylamide gel electrophoresis.

Next, the degradation products of type I collagen were transferred onto a PVDF (polyvinylidene difluoride) membrane by a normal method. Then, an amino acid sequence of an amino terminus of a degradation product of each α 1 chain transferred onto a PVDF membrane was determined by the Edman degradation technique.

Note that APRO Science Inc. or the analyzer collaboration laboratory of the Faculty of Medicine of Kindai University conducted the actual Edman analysis in accordance with a well-known method, at the request of the inventors.

Table 1 shows an amino acid sequence of an amino terminus and the vicinity thereof of a degradation product of an α 1 chain in each of cases where the salt concentration was 0 mM, 200 mM, 1000 mM, 1500 mM, and 2000 mM, respectively.

As shown in Table 1, it was revealed that a cleavage site in an α 1 chain varied depending on the salt concentration. More specifically, it was revealed that a cleavage occurred outside a triple helical domain in a case where the salt concentration was low (for example, 0 mM), and a cleavage occurred inside a triple helical domain in a case where the salt concentration was high (for example, not less than 200 mM).

The cleavage sites observed in cases where the salt concentration was high were novel cleavage sites discovered by the inventors of the present invention.

TABLE 1

| Salt concentration [mM] | Sequence at amino terminus of degradation product of pig-derived α 1 chain | SEQ ID NO: |
|---|---|---|
| 0 | VPGPMGPSGPRG . . . | 2 |
| 200 | MGPSGPRG . . . | 3 |

TABLE 1-continued

| Salt concentration [mM] | Sequence at amino terminus of degradation product of pig-derived α 1 chain | SEQ ID NO: |
|---|---|---|
| 1000 | MGPSGPRG . . . | 3 |
| 1500 | MGPSGPRG . . . | 3 |
| 2000 | MGPSGPRG . . . | 3 |

A ratio of (i) an amount of a degradation product having an amino terminus of the amino acid sequence of SEQ ID NO: 2 among obtained degradation products and (ii) an amount of a degradation product having an amino terminus of the amino acid sequence of SEQ ID NO: 3 among the obtained degradation products varied in accordance with a change in salt concentration. When an attempt was made to prepare degradation products in large quantities, NaCl was insolubilized in a case where the salt concentration exceeded 2000 mM. It is therefore assumed that in a case where degradation products are prepared in large quantities, an upper limit of the salt concentration is preferably set to 500 mM or 800 mM.

2. Influence of Salt Concentration on Cleavage in Rat-Derived and Chicken-Derived α 1 Chains A 50 mM citric acid buffer solution (pH of 3.0) containing sodium chloride at a concentration of 2000 mM was prepared. Water was used as a solvent of this aqueous solution.

For activation of actinidain, actinidain was dissolved in a 50 mM phosphate buffer (pH of 6.5) containing 10 mM dithiothreitol, and a resultant aqueous solution was left to stand at 25° C. for 90 minutes.

Next, rat tail-derived type I collagen or chicken skin-derived type I collagen was dissolved in the 50 mM citric acid buffer solution (pH of 3.0) containing the salt. Rat tail-derived type I collagen or chicken skin-derived type I collagen was caused to be in contact with the aqueous solution containing actinidain and at 20° C. for not shorter than 10 days to prepare degradation products of type I collagen. Note that actinidain was identical to actinidain used in the Example of <1> described above. Rat tail-derived type I collagen and chicken skin-derived type I collagen had each been purified by a well-known method (see, for example, Non Patent Literature 2).

The degradation products of type I collagen thus prepared were separated by polyacrylamide gel electrophoresis.

Next, the degradation products of type I collagen were transferred onto a PVDF (polyvinylidene difluoride) membrane by a normal method. Then, an amino acid sequence of an amino terminus of a degradation product of each α 1 chain transferred onto a PVDF membrane was determined by the Edman degradation technique.

Note that APRO Science Inc. or the analyzer collaboration laboratory of the Faculty of Medicine of Kindai University conducted the actual Edman analysis in accordance with a well-known method, at the request of the inventors.

Table 2 shows (i) an amino acid sequence of an amino terminus and the vicinity thereof of a degradation product of a rat-derived α 1 chain in a case where the salt concentration was 2000 mM and (ii) a partial structure of an undegraded rat-derived α 1 chain (see data indicating "-" in the salt concentration column).

Table 3 shows (i) an amino acid sequence of an amino terminus and the vicinity thereof of a degradation product of a chicken-derived α 1 chain in a case where the salt concentration was 2000 mM and (ii) a partial structure of an undegraded chicken-derived α 1 chain (see data indicating "-" in the salt concentration column).

As shown in Tables 2 and 3, it was revealed that in a case where the salt concentration was high, a cleavage occurred inside a triple helical domain also in α 1 chains derived from different species.

The cleavage sites observed in cases where the salt concentration was high were novel cleavage sites discovered by the inventors of the present invention.

TABLE 2

| Salt concentration [mM] | Sequence at amino terminus of degradation product of rat-derived α 1 chain | SEQ ID NO: |
|---|---|---|
| — | SAGVSVPGPMGPSGPR . . . | 4 |
| 2000 | MGPSGPR . . . | 5 |

TABLE 3

| Salt concentration [mM] | Sequence at amino terminus of degradation product of chicken-derived α 1 chain | SEQ ID NO: |
|---|---|---|
| — | SAGVAVPGPMGPAGPRG . . . | 6 |
| 2000 | GPAGPRG . . . | 7 |

<3. Consideration Regarding Salt Type>

An aqueous solution containing $MgCl_2$ at a concentration of 500 mM and an aqueous solution containing KCl at a concentration of 200 mM were prepared. Water was used as a solvent of these aqueous solutions.

Actinidain and pig-derived type I collagen were mixed with each of the aqueous solutions, and then resultant mixtures were each left to react at 20° C. for not shorter than 10 days to prepare degradation products of type I collagen. Note that actinidain was identical to actinidain used in the Example of <1> described above. Pig-derived type I collagen had been purified by a well-known method (see, for example, Non Patent Literature 2).

The degradation products thus prepared were subjected to polyacrylamide gel electrophoresis to separate degradation products of α 1 chains.

Next, the degradation products of type I collagen were transferred onto a PVDF (polyvinylidene difluoride) membrane by a normal method. Then, an amino acid sequence of an amino terminus of a degradation product of each α 1 chain transferred onto a PVDF membrane was determined by the Edman degradation technique.

Note that APRO Science Inc. or the analyzer collaboration laboratory of the Faculty of Medicine of Kindai University conducted the actual Edman analysis in accordance with a well-known method, at the request of the inventors.

Table 4 shows (i) an amino acid sequence of an amino terminus and the vicinity thereof of a degradation product of a pig-derived α 1 chain in each of a case where the aqueous solution containing $MgCl_2$ at a concentration of 500 mM was used and a case where the aqueous solution containing KCl at a concentration of 200 mM was used and (ii) a partial structure of an undegraded pig-derived α 1 chain (see data indicating "-" in the salt concentration column).

As shown in Table 4, it was revealed that a cleavage occurred inside a triple helical domain also in cases where different salts were used.

The cleavage sites observed in the cases where the different salts were used were novel cleavage sites discovered by the inventors of the present invention.

TABLE 4

| Salt concentration [mM] | Sequence at amino terminus of degradation product of pig-derived α 1 chain | SEQ ID NO: |
|---|---|---|
| — | ISVPGPMGPSGPRG . . . | 8 |
| 200 (KCl) | MGPSGPRG . . . | 9 |
| 500 ($MgCl_2$) | MGPSGPRG . . . | 9 |

<4. Consideration Regarding Cysteine Protease Type>

In this Example, cathepsin K, which is a kind of cysteine protease, was used to consider a cleavage site of an α 1 chain under a high salt concentration condition. The following describes a test method and test results.

A 50 mM citric acid buffer solution (pH of 3.0) containing sodium chloride at a concentration of 2000 mM was prepared. Water was used as a solvent of this aqueous solution.

For activation of cathepsin K, cathepsin K was dissolved in a 50 mM phosphate buffer (pH of 6.5) containing 10 mM dithiothreitol, and a resultant aqueous solution was left to stand at 25° C. for 45 minutes. Note that cathepsin K was commercially available cathepsin K.

Next, chicken-derived type I collagen or pig-derived type I collagen was dissolved in the 50 mM citric acid buffer solution (pH of 3.0) containing the salt. A resultant solution containing chicken-derived type I collagen or pig-derived type I collagen was caused to be in contact with the aqueous solution containing cathepsin K at 20° C. for not shorter than 10 days to prepare degradation products of type I collagen. Note that chicken-derived type I collagen and pig-derived type I collagen had each been purified by a well-known method (see, for example, Non Patent Literature 2).

The prepared degradation products of type I collagen thus prepared were separated by polyacrylamide gel electrophoresis.

Next, the degradation products of type I collagen were transferred onto a PVDF (polyvinylidene difluoride) membrane by a normal method. Then, an amino acid sequence of an amino terminus of a degradation product of each α 1 chain transferred onto a PVDF membrane was determined by the Edman degradation technique.

Note that APRO Science Inc. or the analyzer collaboration laboratory of the Faculty of Medicine of Kindai University conducted the actual Edman analysis in accordance with a well-known method, at the request of the inventors.

Table 5 shows (i) an amino acid sequence of an amino terminus and the vicinity thereof of a degradation product of a pig-derived α 1 chain and (ii) a partial structure of an undegraded pig-derived α 1 chain (see data indicating "-" in the salt concentration column).

As shown in Table 5, it was revealed that, also in a case where cathepsin K, which is a kind of cysteine protease, was used, a cleavage occurred inside a triple helical domain when the salt concentration was high.

Further, as shown in Table 5, a plurality of kinds of cleavage sites were observed in the case where cathepsin K, which is a kind of cysteine protease, was used.

Note that in a case of a degradation product of chicken-derived type I collagen, the following degradation products of chicken-derived α 1 chains were observed: (i) a degradation product of a chicken-derived α 1 chain which degradation product corresponds to SEQ ID NO: 11 below, (ii) a degradation product of a chicken-derived α 1 chain which degradation product corresponds to SEQ ID NO: 12 below, and (iii) degradation products of a chicken-derived α 1 chain which degradation products correspond to portions obtainable by cleavage of a chemical bond between "S" and "G" located in the respective 10th and 11th positions as counted from an amino terminus of SEQ ID NO: 10.

TABLE 5

| Salt concentration [mM] | Sequence at amino terminus of degradation product of pig-derived α 1 chain | SEQ ID NO: |
|---|---|---|
| — | ISVPGPMGPSGPRGLPGP PGAPGPQGFQG . . . | 10 |
| 2000 | GLPGPPGAPGPQG FQG . . . | 11 |
| 2000 | GFQG . . . | 12 |

<5. Influence of Dialysis Salt Concentration on Cleavage in Pig-Derived α 1 Chain>

Actinidain was supplied to a dialysis tube and dialyzed against a dialysis outer liquid containing sodium chloride at a concentration of 2000 mM. Then, the dialysis was continued with distilled water in place of the dialysis outer liquid to obtain actinidain. Note that actinidain had been purified by a well-known method (see, for example, Non Patent Literature 2). For activation of actinidain, actinidain was dissolved in a 50 mM phosphate buffer (pH of 6.5) containing 10 mM dithiothreitol, and a resultant aqueous solution was left to stand at 25° C. for 90 minutes.

Next, pig-derived type I collagen was dissolved in a 50 mM citric acid buffer solution (pH of 3.0) containing a salt. Pig-derived type I collagen was caused to be in contact with the aqueous solution containing actinidain at 20° C. for not shorter than 3 days to prepare a degradation product of type I collagen. Note that pig-derived type I collagen had been purified by a well-known method (see, for example, Non Patent Literature 2).

The degradation product of type I collagen thus prepared was separated by polyacrylamide gel electrophoresis.

Next, the degradation product of type I collagen was transferred onto a PVDF (polyvinylidene difluoride) membrane by a normal method. Then, an amino acid sequence of an amino terminus of a degradation product of an α 1 chain transferred onto the PVDF membrane was determined by the Edman degradation technique.

Note that APRO Science Inc. or the analyzer collaboration laboratory of the Faculty of Medicine of Kindai University conducted the actual Edman analysis in accordance with a well-known method, at the request of the inventors.

Table 6 shows (i) an amino acid sequence of an amino terminus and the vicinity thereof of a degradation product of a pig-derived α 1 chain in a case where the dialysis salt concentration was 2000 mM and (ii) a partial structure of an undegraded pig-derived α 1 chain (see data indicating "-" in the salt concentration column).

As shown in Table 6, it was revealed that a cleavage occurred inside a triple helical domain in a case where the dialysis salt concentration was high.

The cleavage site observed in the case where the salt concentration was high was a novel cleavage site discovered by the inventors of the present invention.

TABLE 6

| Salt concentration [mM] | Sequence at amino terminus of degradation product of pig-derived α 1 chain | SEQ ID NO: |
|---|---|---|
| — | ISVPGPMGPSGPRGLPGP PGAPGPQGFQG . . . | 10 |
| 2000 | LPGPPGAPGPQGF GQG . . . | 15 |

<6. Influence of Dialysis Salt Concentration on Cleavage in Human-Derived α 1 Chain>

Actinidain was supplied to a dialysis tube and dialyzed against a dialysis outer liquid containing sodium chloride at a concentration of 2000 mM. Then, the dialysis was continued with distilled water in place of the dialysis outer liquid to obtain actinidain. Note that actinidain had been purified by a well-known method (see, for example, Non Patent Literature 2). For activation of actinidain, actinidain was dissolved in a 50 mM phosphate buffer (pH of 6.5) containing 10 mM dithiothreitol, and a resultant aqueous solution was left to stand at 25° C. for 90 minutes.

Next, human-derived type I collagen was dissolved in a 50 mM citric acid buffer solution (pH of 3.5) containing a salt. Human-derived type I collagen was caused to be in contact with the aqueous solution containing actinidain at 20° C. for not shorter than 10 days to prepare a degradation product of type I collagen. Note that human-derived type I collagen had been purified by a well-known method (see, for example, Non Patent Literature 2).

The degradation product of type I collagen thus prepared was separated by polyacrylamide gel electrophoresis.

Next, the degradation product of type I collagen was transferred onto a PVDF (polyvinylidene difluoride) membrane by a normal method. Then, an amino acid sequence of an amino terminus of a degradation product of an α 1 chain transferred onto the PVDF membrane was determined by the Edman degradation technique.

Note that APRO Science Inc. or the analyzer collaboration laboratory of the Faculty of Medicine of Kindai University conducted the actual Edman analysis in accordance with a well-known method, at the request of the inventors.

As shown in Table 7, it was revealed that a cleavage occurred inside a triple helical domain in a case where the dialysis salt concentration was high.

The cleavage site observed in the case where the salt concentration was high was a novel cleavage site discovered by the inventors of the present invention.

TABLE 7

| Salt concentration [mM] | Sequence at amino terminus of degradation product of human-derived α 1 chain | SEQ ID NO: |
|---|---|---|
| 2000 | LPGPP . . . | 16 |

<7. Cleavage in Fish-Derived α 1 Chain>

Actinidain was supplied to a dialysis tube and dialyzed against a dialysis outer liquid containing sodium chloride at a concentration of 2000 mM. Then, the dialysis was continued with distilled water in place of the dialysis outer liquid to obtain actinidain. For activation of actinidain, actinidain was dissolved in a 50 mM phosphate buffer (pH of 6.5) containing 10 mM dithiothreitol, and a resultant aqueous solution was left to stand at 25° C. for 90 minutes.

Next, fish-derived (specifically, yellowfin tuna-derived) type I collagen was dissolved in a 50 mM citric acid buffer solution (pH of 3.0) containing a salt. Fish-derived type I collagen was caused to be in contact with the aqueous solution containing actinidain at 20° C. for not shorter than 3 days to prepare a degradation product of type I collagen. Note that actinidain was identical to actinidain used in the Example of <1> described above. Fish-derived type I collagen had been purified by a well-known method (see, for example, Non Patent Literature 2).

The degradation product of type I collagen thus prepared was separated by polyacrylamide gel electrophoresis.

Next, the degradation product of type I collagen was transferred onto a PVDF (polyvinylidene difluoride) membrane by a normal method. Then, an amino acid sequence of an amino terminus of a degradation product of an α 1 chain (fish-derived type I collagen) transferred onto the PVDF membrane was determined by the Edman degradation technique.

Note that APRO Science Inc. or the analyzer collaboration laboratory of the Faculty of Medicine of Kindai University conducted the actual Edman analysis in accordance with a well-known method, at the request of the inventors.

Table 8 shows (i) an amino acid sequence of an amino terminus and the vicinity thereof of a degradation product of a fish-derived α 1 chain in a case where the dialysis outer liquid had a salt concentration of 2000 mM. As shown in Table 8, two kinds of degradation products were detected as the degradation product of the α 1 chain (fish-derived type I collagen), and amino acid sequences of SEQ ID NO: 18 and 19 were successfully identified as amino acid sequences of amino terminuses of the respective degradation products.

TABLE 8

| | Sequence at amino terminus of degradation product of fish-derived α 1 chain | SEQ ID NO: |
|---|---|---|
| Fish-derived type I collagen (α 1), no enzyme | MAVPGPMGPMGPRGAPG PPGP . . . | 17 |
| Fish-derived type I collagen (α 1) | MGPRGAPGPPGPS GPQG . . . | 18 |
| Fish-derived type I collagen (α 1) | SGPQG . . . | 19 |

<8. Cleavage in Human-Derived α 2 Chain>

As in <4>, for activation of cathepsin K, cathepsin K was dissolved in a 50 mM phosphate buffer (pH of 6.5) containing 10 mM dithiothreitol, and a resultant aqueous solution was left to stand at 25° C. for 45 minutes.

Next, human-derived type I collagen was dissolved in a 50 mM phosphate buffer (pH of 6.0) containing a salt. Human-derived type I collagen was caused to be in contact with the aqueous solution containing cathepsin K at 20° C. for not shorter than 10 days to prepare a degradation product of type I collagen. Note that cathepsin K was identical to cathepsin K used in the example of <1> described above. Human-derived type I collagen had been purified by a well-known method (see, for example, Non Patent Literature 2).

The prepared degradation product of type I collagen thus prepared was separated by polyacrylamide gel electrophoresis.

Next, the degradation product of type I collagen was transferred onto a PVDF (polyvinylidene difluoride) membrane by a normal method. Then, an amino acid sequence of an amino terminus of a degradation product of an α 2 chain (human-derived type I collagen) transferred onto the PVDF membrane was determined by the Edman degradation technique.

Note that APRO Science Inc. or the analyzer collaboration laboratory of the Faculty of Medicine of Kindai University conducted the actual Edman analysis in accordance with a well-known method, at the request of the inventors.

Table 9 shows (i) an amino acid sequence of an amino terminus and the vicinity thereof of a degradation product of a human-derived α 2 chain in a case where a reaction liquid had a salt concentration of 200 mM.

TABLE 9

| | Sequence at amino terminus of degradation product of human-derived α 2 chain | SEQ ID NO: |
|---|---|---|
| Human-derived type I collagen (α 2), no enzymatic treatment | QYDGKGVGLGPGPMGLMGPRGPPGA . . . | 20 |
| Human-derived type I collagen (α 2) | GPRGPPGA . . . | 21 |

<9. Cleavage in Chicken-Derived α 2 Chain>

Actinidain was supplied to a dialysis tube and dialyzed against a dialysis outer liquid containing sodium chloride at a concentration of 2000 mM. Then, the dialysis was continued with distilled water in place of the dialysis outer liquid to obtain actinidain. For activation of actinidain, actinidain was dissolved in a 50 mM phosphate buffer (pH of 6.5) containing 10 mM dithiothreitol, and a resultant aqueous solution was left to stand at 25° C. for 90 minutes.

Next, chicken-derived type I collagen was dissolved in a 50 mM citric acid buffer solution (pH of 3.0) containing a salt. Chicken-derived type I collagen was caused to be in contact with the aqueous solution containing actinidain at 20° C. for not shorter than 7 days to prepare a degradation product of type I collagen. Note that actinidain was identical to actinidain used in the Example of <1> described above. Chicken-derived type I collagen had been purified by a well-known method (see, for example, Non Patent Literature 2).

The degradation product of type I collagen thus prepared was separated by polyacrylamide gel electrophoresis.

Next, the degradation product of type I collagen was transferred onto a PVDF (polyvinylidene difluoride) membrane by a normal method. Then, an amino acid sequence of an amino terminus of a degradation product of an α 2 chain (chicken-derived type I collagen) transferred onto the PVDF membrane was determined by the Edman degradation technique.

Note that APRO Science Inc. or the analyzer collaboration laboratory of the Faculty of Medicine of Kindai University conducted the actual Edman analysis in accordance with a well-known method, at the request of the inventors.

Table 10 shows (i) an amino acid sequence of an amino terminus and the vicinity thereof of a degradation product of a chicken-derived α 2 chain in a case where the dialysis outer liquid had a salt concentration of 2000 mM.

TABLE 10

| | Sequence at amino terminus of degradation product of human-derived α 2 chain | SEQ ID NO: |
|---|---|---|
| Chicken-derived type I collagen (α 2), no enzymatic treatment | QYDPSKAADFGPGPMGL MGPRGPPGAS . . . | 22 |
| Chicken-derived type I collagen (α 2) | GPRGPPGAS . . . | 23 |

As shown in the tables, it was revealed that a high salt concentration results in a cleavage occurring inside a triple helical domain also in an α 1 chain or an α 2 chain derived from a different species. The cleavage site observed in a case where the salt concentration was high was a novel cleavage site discovered by the inventors of the present invention.

<10. Test Regarding Spheroid-Inducing Ability of Degradation Product of Collagen—1>

Commercially available culture plates which were caused to be in contact with a collagen degradation product described above (a degradation product of a pig-derived α 1 chain obtained in a case of a salt concentration of 200 mM) were used in a test.

Cells (mouse preosteoblast cell strains MC3T3-E1 subclone 4) were seeded in each culture plate and cultured under the condition of 37° C. and 5% $CO_2$.

Cells after an elapse of a predetermined time period from the start of the culture were observed with a microscope. Photomicrographs of the cells are shown in FIGS. 1 through 7.

Figure 1:
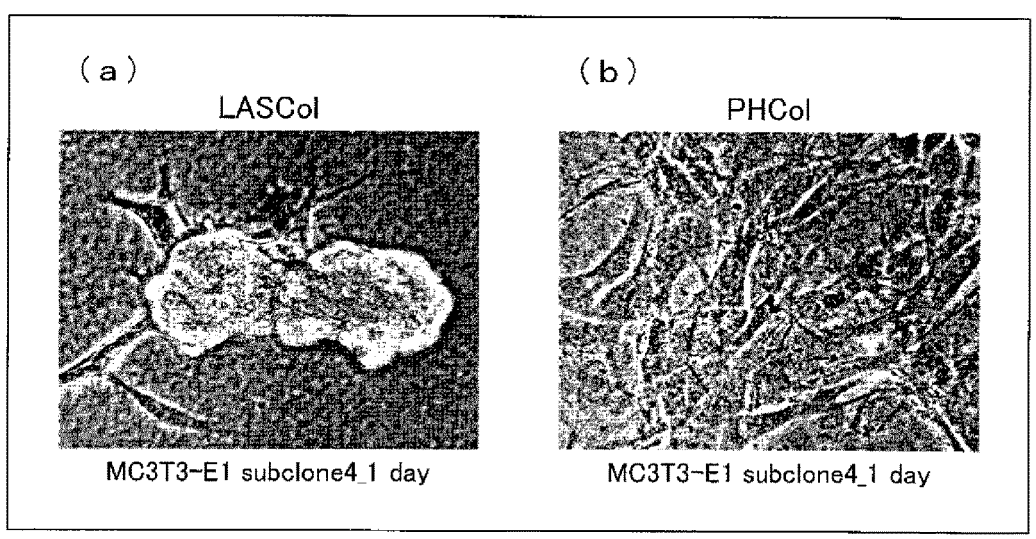

Specifically, (a) and (b) of FIG. 1 each show a photomicrograph of mouse preosteoblast cell strains MC3T3-E1 subclone 4 (ATCC® CRL-2593, Summit Pharmaceutical International).

In FIG. 1, "PHCol" shows a result of a culture plate which was caused to be in contact with a commercially available and pepsin-treated type I collagen, and "LASCol" shows a result of a culture plate which was caused to be in contact with the collagen degradation product of this Example.

In FIG. 1, a time period indicated in each of (a) and (b) of FIG. 1 represents a culture time period.

As is clear from FIG. 1, it was revealed that the collagen degradation product of this Example had a spheroid-inducing ability.

<11. Test Regarding Spheroid-Inducing Ability of Degradation Product of Collagen—2>

Commercially available culture plates which were caused to be in contact with a collagen degradation product described above (a degradation product of a pig-derived α 1 chain obtained in a case of a salt concentration of 200 mM) were used in a test.

Cells (mouse fibroblast strains NIH/3T3 (RBRC-RCB2767, RIKEN Bio Resource Center)) were seeded in each culture plate and cultured under the condition of 37° C. and 5% $CO_2$.

Figure 2:
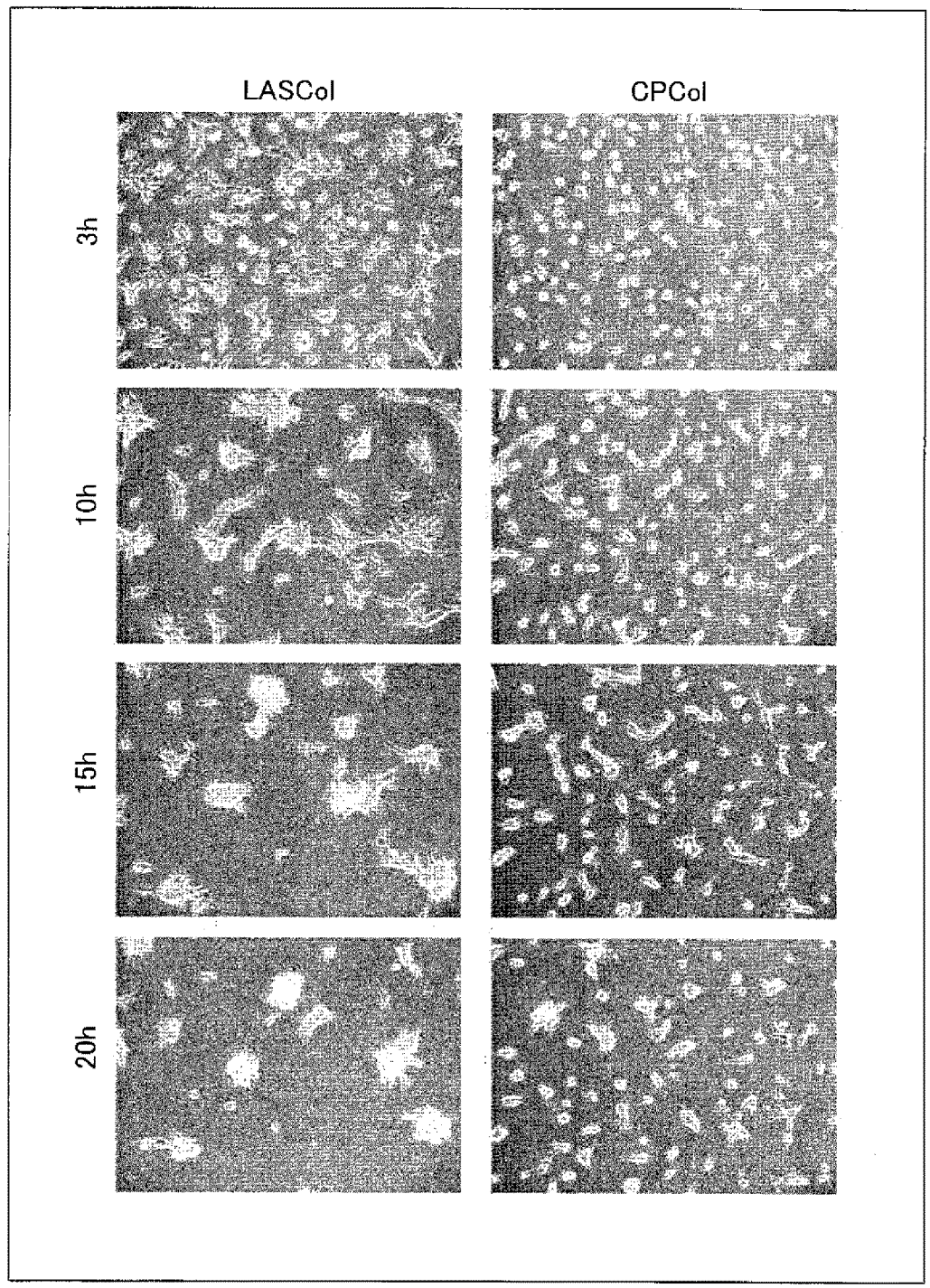
FIG. 2 shows photomicrographs of a spheroid of a mouse fibroblast NIH/3T3, which was induced by a degradation product of an Example of the present invention.

Cells after an elapse of a predetermined time period from the start of the culture were observed with a microscope. Photomicrographs of the cells are shown in FIG. 2. In FIG. 2, "LASCol" shows a result of a culture plate which was caused to be in contact with the collagen degradation product of this Example, and "CPCol" shows a result of a culture plate which was caused to be in contact with a conventional collagen degradation product (see WO2004/020470).

As is clear from FIG. 2, it was revealed that the collagen degradation product of this Example was capable not only of forming a spheroid earlier but also of forming a larger spheroid, as compared with the conventional collagen degradation product.

<12. Test Regarding Differentiation-Inducing Ability—1>

A commercially available culture plate (micro dish 35 mm (μ-Dish 35 mm) uncoated, Cat. #: ib81151, NIPPON Genetics Co., Ltd) which was caused to be in contact with a collagen degradation product described in <1> above was used in a test.

As control tests, the following three kinds of culture plates were used: a culture plate (ibidi μ-Dish 35 mm uncoated, Cat. #: ib81151, NIPPON Genetics Co., Ltd) which was caused to be in contact with a commercially available and pepsin-treated type I collagen (Cellmatrix® Type I-C, Nitta Gelatin Inc.), a culture plate (ibidi μ-Dish 35 mm surface-treated ibiTreat, Cat. #: ib81156, NIPPON Genetics Co., Ltd) which was not caused to be in contact with a collagen degradation product, and commercially available Nano Culture® Dish MH pattern (Cat. #: NCD-LH35-5, SCIVAX Corporation).

The following describes a test method and test results

First, mouse preosteoblast cell strains MC3T3-E1 subclone 4 (ATCC® CRL-2593, Summit Pharmaceutical International) suspended in a basal medium (α-MEM, 10% FBS) were seeded in each of the four kinds of culture plates described above, and then were cultured under the condition of 37° C. and 5% $CO_2$ for 24 hours.

After 24 hours of culture, the basal medium in the culture plate was fully substituted with an osteoblast differentiation-inducing culture medium (α-MEM, 10% FBS, 50μ g-ascorbic acid/mL, 3.5 mM β-glycerophosphate).

The culture was continued while the osteoblast differentiation-inducing culture medium in the culture plate was substituted with a fresh osteoblast differentiation-inducing culture medium every 3 days.

10 days, 14 days, or 21 days after the basal medium in the culture plate was substituted with an osteoblast differentiation-inducing culture medium, mouse preosteoblast cell strains MC3T3-E1 subclone 4 were stained using an alizarin red staining kit (product No. ARD-A1, Kabushiki Kaisha PG Research) to check whether or not mineralization of the mouse preosteoblast cell strains MC3T3-E1 subclone 4 had occurred. Note that the alizarin red staining was conducted in accordance with a well-known method.

Figure 3:
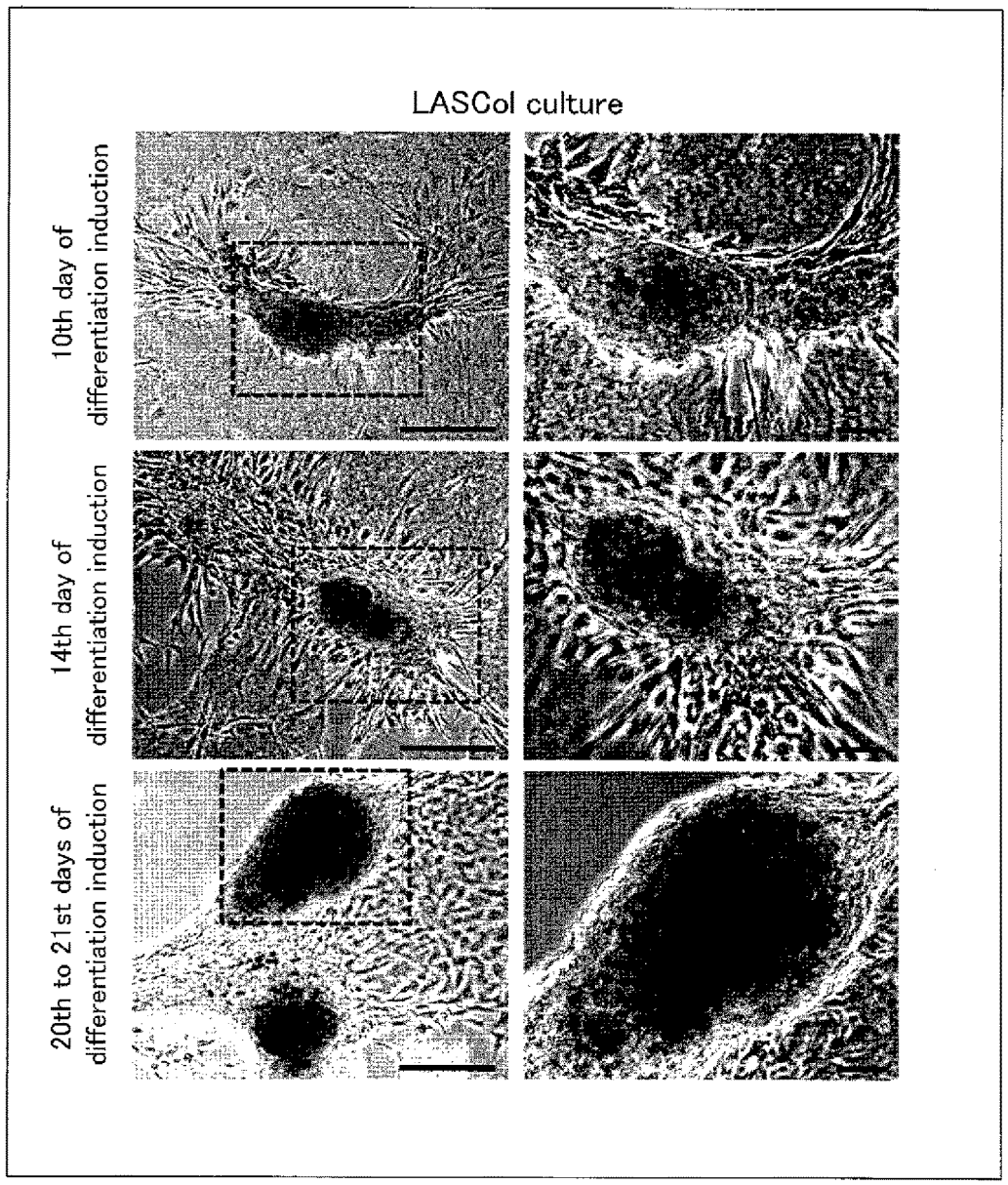
FIG. 3 shows photographs of stained results of alizarin red staining which was conducted in the case of using a commercially available culture plate caused to be in contact with a degradation product of an Example of the present invention.
Figure 4:
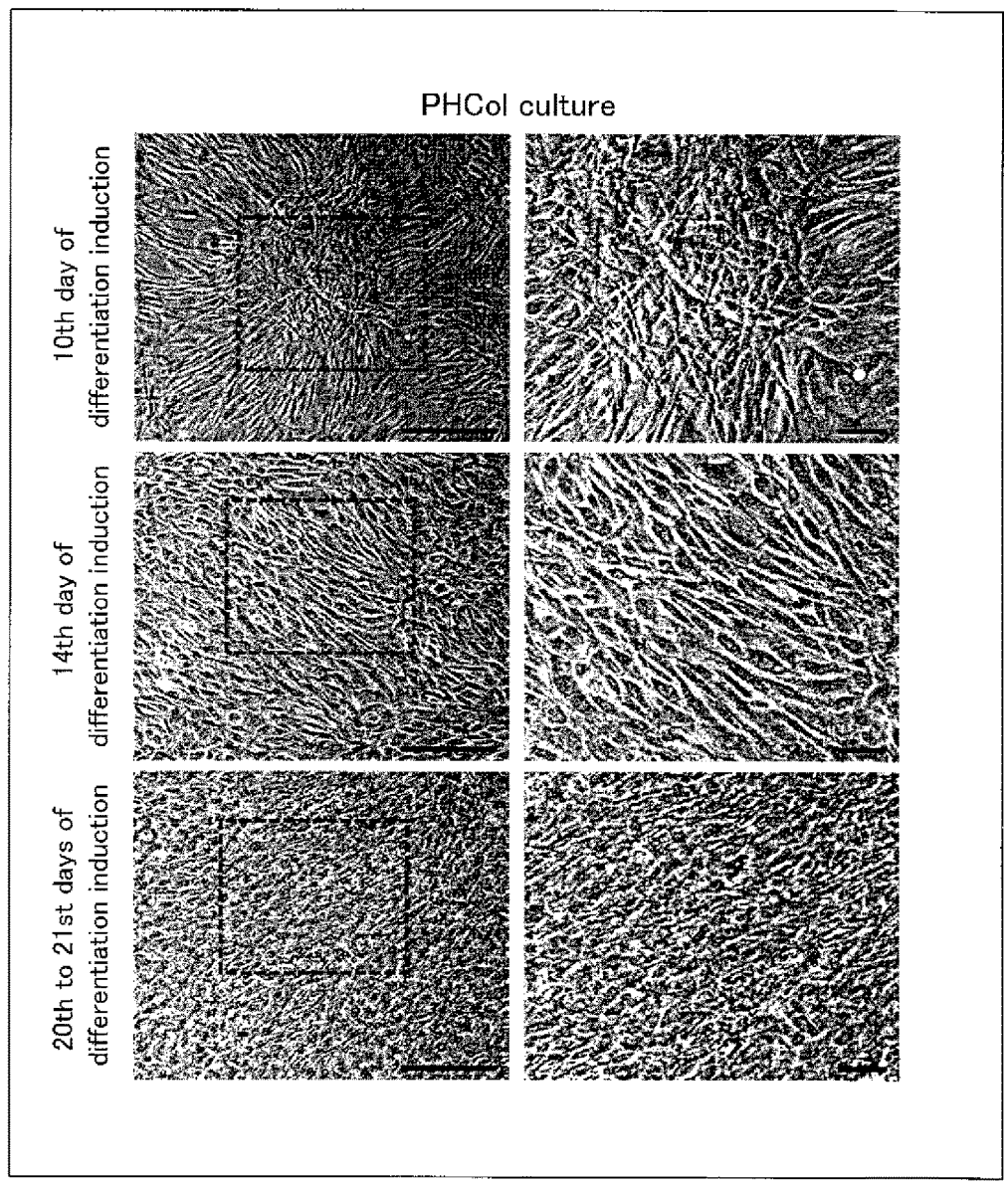
FIG. 4 shows photographs of stained results of alizarin red staining which was conducted in the case of using a culture plate which was caused to be in contact with a commercially available pepsin-treated type I collagen.
Figure 5:
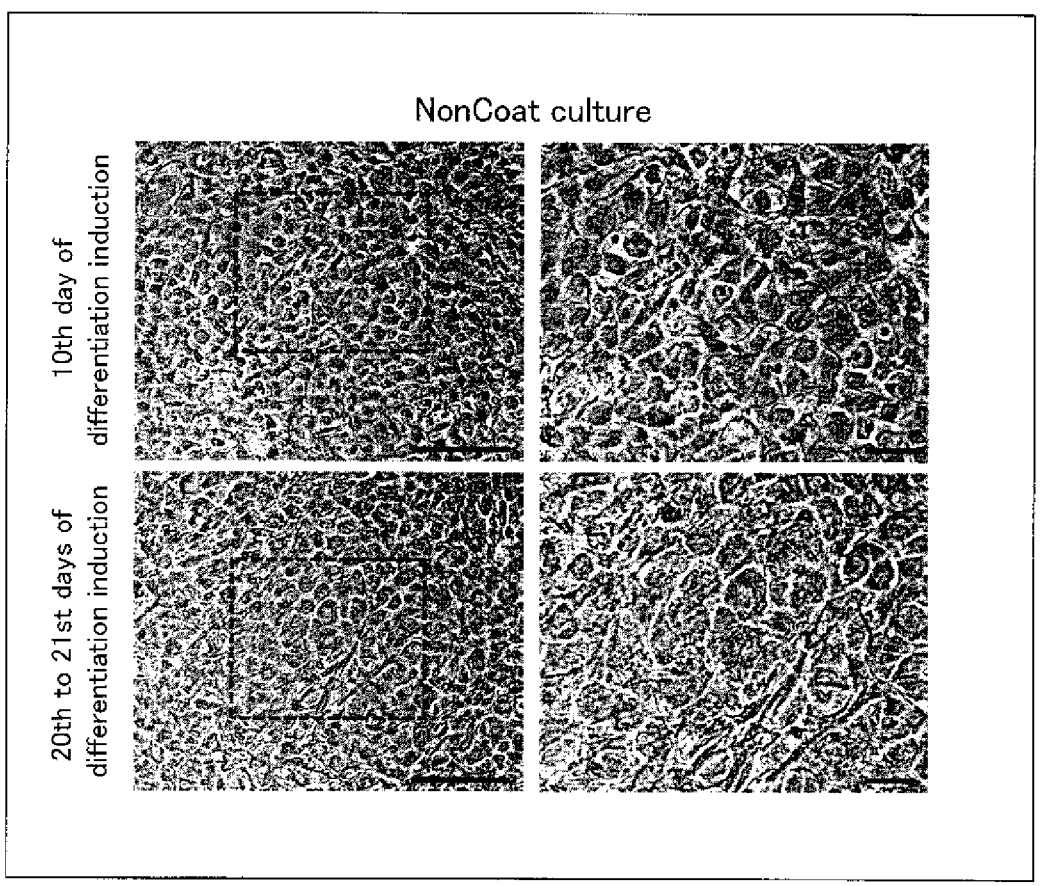
FIG. 5 shows photographs of stained results of alizarin red staining which was conducted in the case of using a culture plate which was not caused to be in contact with a degradation product of collagen.
Figure 6:
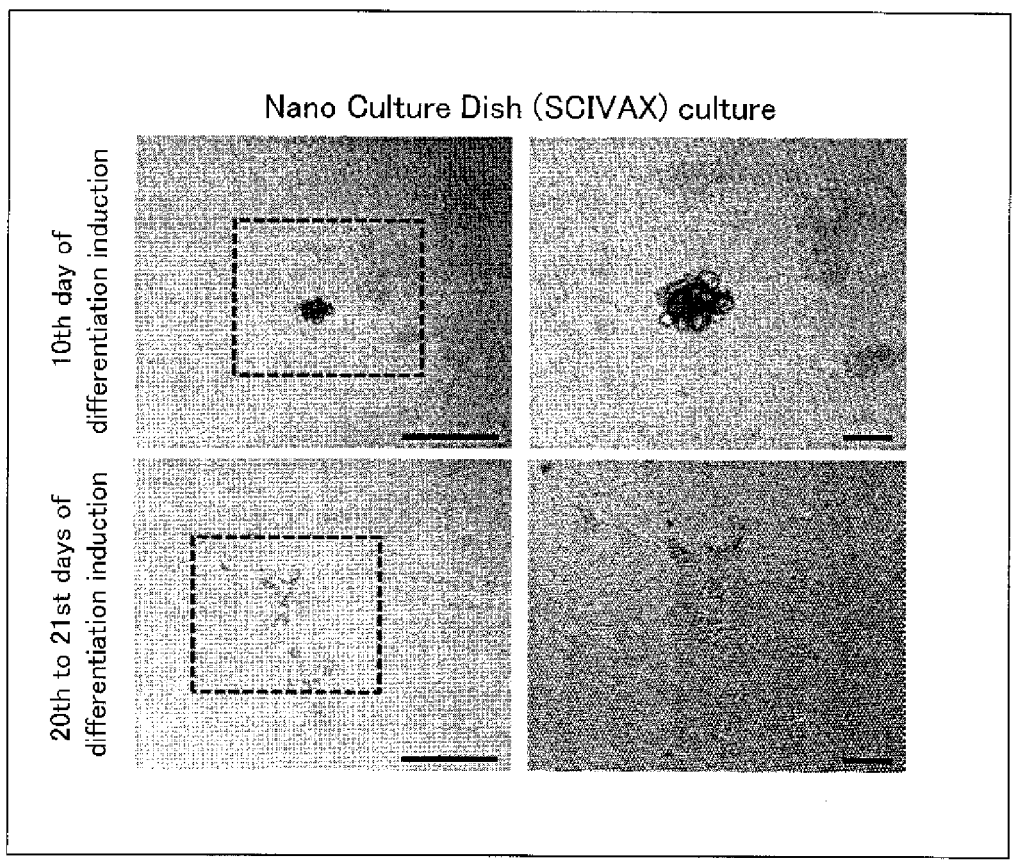
FIG. 6 shows photographs of stained results of alizarin red staining which was conducted in the case of using commercially available Nano Culture Dish (SCIVAX Corporation).

FIGS. 3 through 6 each show a result of the alizarin red staining. Specifically, FIG. 3 shows photographs of stained results of alizarin red staining which was conducted in the case of using the commercially available culture plate caused to be in contact with the collagen degradation product described in <1> above, FIG. 4 shows photographs of stained results of alizarin red staining which was conducted in the case of using the culture plate caused to be in contact with the commercially available and pepsin-treated type I collagen, FIG. 5 shows photographs of stained results of alizarin red staining which was conducted in the case of using the culture plate not caused to be in contact with a collagen degradation product, and FIG. 6 shows photographs of stained results of alizarin red staining which was conducted in the case of using commercially available Nano Culture Dish (SCIVAX Corporation).

As shown in FIG. 3, in the case of using the commercially available culture plate which was caused to be in contact with the collagen degradation product described in <1> above, a part near the center of a spheroid was stained red and thus cell mineralization was observed, 10 days after the basal medium in the culture plate was substituted with the osteoblast differentiation-inducing culture medium.

The amount of mineralization increased as the number of days of inducing differentiation increased. No mineralization was observed in cells other than the spheroid of the present application. That is, it was shown that the collagen degradation product described in <1> above promoted cell mineralization.

Meanwhile, as shown in FIGS. 4 through 6, no cell was stained in the three kinds of culture plates serving as the control tests, 21 days after substitution of a basal medium with an osteoblast differentiation-inducing culture medium in the culture plates. That is, in each of the three kinds of culture plates serving as the control tests, no cell mineralization was observed 21 days after substitution of a basal medium with an osteoblast differentiation-inducing culture medium in the culture plate.

In particular, in the case where commercially available Nano Culture Dish (SCIVAX Corporation) was used, substitution of a culture medium every 3 days caused a large number of cells to float away from the culture plate. Then, 21 days after substitution of a basal medium with an osteoblast differentiation-inducing culture medium in the culture plate, 80% to 90% of the seeded cells had been lost. Also in the process of alizarin red staining treatment, a large number of cells floated away from the culture plate and were lost.

<13. Test Regarding Differentiation-Inducing Ability—2>

A commercially available culture plate which was caused to be in contact with a collagen degradation product described in <1> above was used in a test.

As control tests, a culture plate which was caused to be in contact with a commercially available and pepsin-treated type I collagen, a commercially available culture plate (a culture plate which was caused to be in contact with a pepsin-treated pig tendon-derived type I collagen: product No. 4000-010, produced by IWAKI Cytec), and a culture plate which was not caused to be in contact with a collagen degradation product were used.

The following describes a test method and test results.

First, rat bone marrow mesenchymal stem cells (BMC01: Primary Cell Co., Ltd) suspended in a bone marrow cell culture medium (BMCM: Primary Cell Co., Ltd) were seeded in each of the four kinds of culture plates described above, and then were cultured under the condition of 37° C. and 5% $CO_2$ for 24 hours.

After 24 hours of culture, the bone marrow cell culture medium in the culture plate was fully substituted with an osteogenesis culture medium (OGCMO: Primary Cell Co., Ltd).

The culture was continued while the osteogenesis culture medium in the culture plate was substituted with a fresh osteogenesis culture medium every 3 days.

After the bone marrow cell culture medium in the culture plate was substituted with an osteogenesis culture medium, rat bone marrow mesenchymal stem cells were stained over time by alizarin red staining to check whether or not mineralization of the rat bone marrow mesenchymal stem cells had occurred. Note that the alizarin red staining was conducted in accordance with a well-known method.

Figure 7:
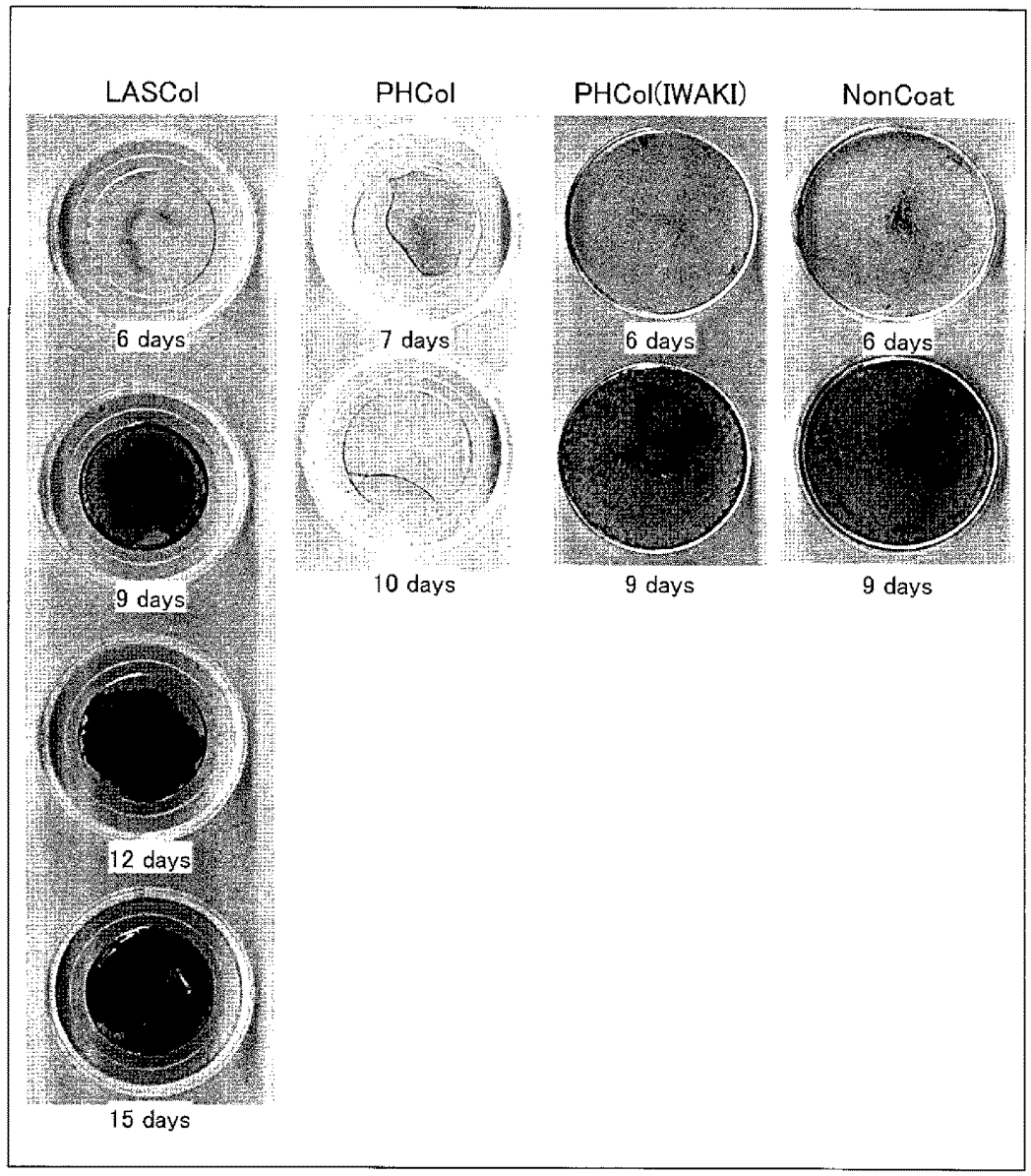
FIG. 7 shows photographs of stained results of alizarin red staining which was conducted in the case of various kinds of culture plates.

FIG. 7 shows results of the alizarin red staining. Specifically, "LASCol" in FIG. 7 shows photographs of stained results of alizarin red staining which was conducted in the case of using the commercially available culture plate caused to be in contact with the collagen degradation product described in <1> above, "PHCol" in FIG. 7 shows photographs of stained results of alizarin red staining which was conducted in the case of using the culture plate caused to be in contact with the commercially available and pepsin-treated type I collagen, "PHCol(IWAKI)" in FIG. 7 shows photographs of stained results of alizarin red staining which was conducted in the case of using the commercially available culture plate (produced by IWAKI Cytec), and "Non-Coat" in FIG. 7 shows photographs of stained results of alizarin red staining which was conducted in the case of using the culture plate not caused to be in contact with a collagen degradation product.

A significant mineralization was observed in "LASCol" 9 days after replacement of the culture medium. Microscopic observation of the classification showed that "LASCol" had significantly less cells that are present on the culture plate, as compared with "PHCol(IWAKI)" and "NonCoat." This means that "LASCol" has a significantly high mineralization ability per cell as compared with "PHCol(IWAKI)" and "NonCoat."

Further, "LASCol" exhibited a significant increase in staining intensity on the entire culture plate as the culture time period increased (see, for example, "12 days" and "15 days" in FIG. 7).

Meanwhile, "PHCol" showed a tendency in which a pepsin-treated type I collagen on the surface of the culture plate peeled off 3 days after the start of the culture. No mineralization was observed in "PHCol" both 7 days and 10 days after the substitution of the culture medium.

Each of "PHCol(IWAKI)" and "NonCoat" had a slight mineralization which was observed 6 days after the substitution of the culture medium, and showed a tendency in which the mineralization was slightly promoted 9 days after the substitution of the culture medium.

<14. Test Regarding Differentiation-Inducing Ability—3>

A commercially available culture plate (ibidi μ-Dish (uncoated), NIPPON Genetics Co., Ltd) which was caused to be in contact with a collagen degradation product described in <1> above was used in a test.

As control tests, the following two kinds of culture plates were used: a culture plate (ibidi μ-Dish (uncoated), NIPPON Genetics Co., Ltd) which was caused to be in contact with a commercially available and pepsin-treated type I collagen (Cellmatrix® Type I-C, Nitta Gelatin Inc.) and a culture plate (ibidi μ-Dish (uncoated), NIPPON Genetics Co., Ltd) which was not caused to be in contact with a collagen degradation product.

The same number of rat bone marrow mesenchymal stem cells were seeded in each culture plate.

The culture medium in each culture plate was substituted with an osteoblast differentiation culture medium (produced by the Primary Cell Division of COSMO BIO Co., Ltd) every few days.

11 days after the sowing, cells in each culture plate were fixed using a glutaraldehyde solution.

After the cells were dewatered according to a normal method, each culture plate was observed with a scanning electron microscope (SEM) (manufactured by Hitachi High-Technologies Corporation, SU3500) and was also subjected to an elemental analysis.

Figure 8:
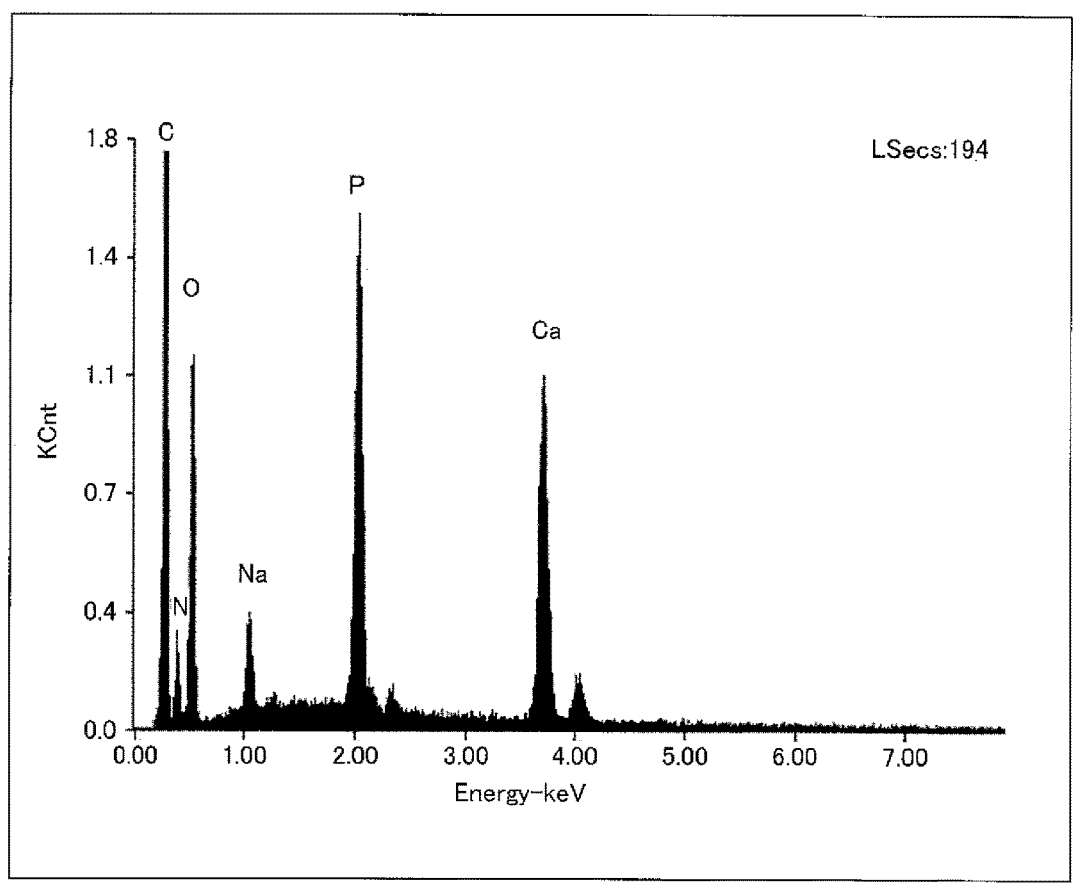
FIG. 8 shows a graph that shows a result of a cell elemental analysis in the case of using a commercially available culture plate which was caused to be in contact with a degradation product of an Example of the present invention.
Figure 9:
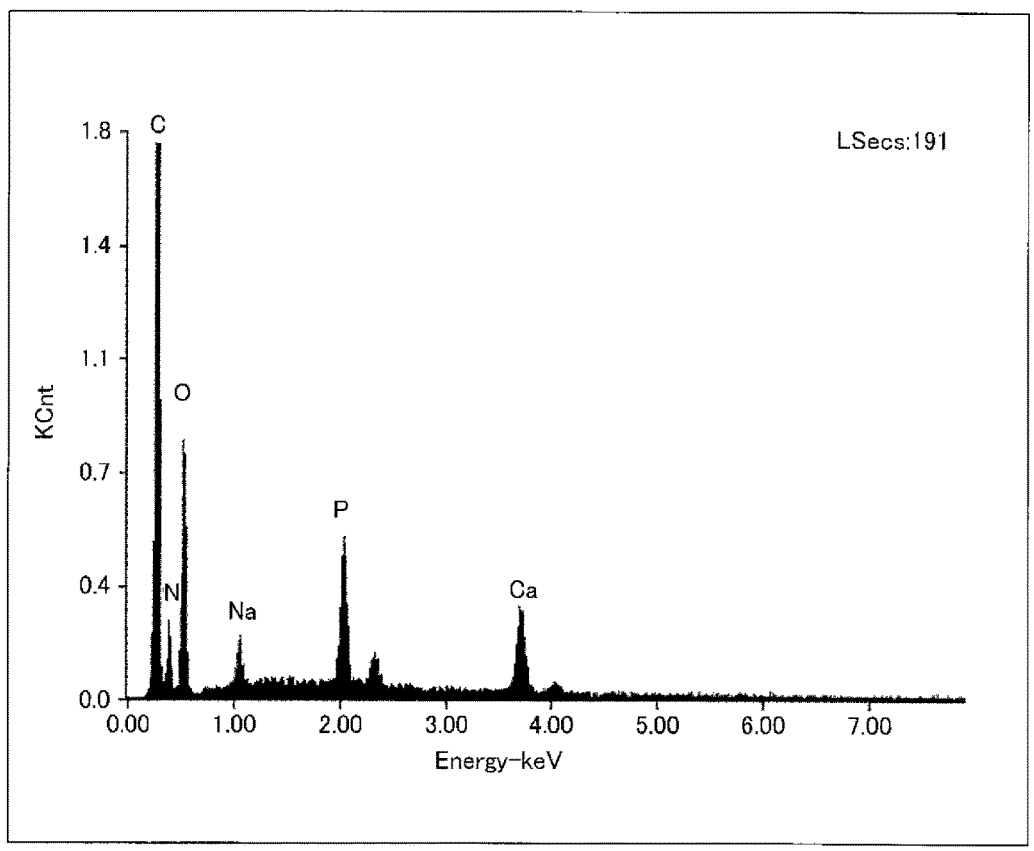
FIG. 9 shows a graph that shows a result of a cell elemental analysis in the case of using a culture plate which was caused to be in contact with a commercially available pepsin-treated type I collagen.
Figure 10:
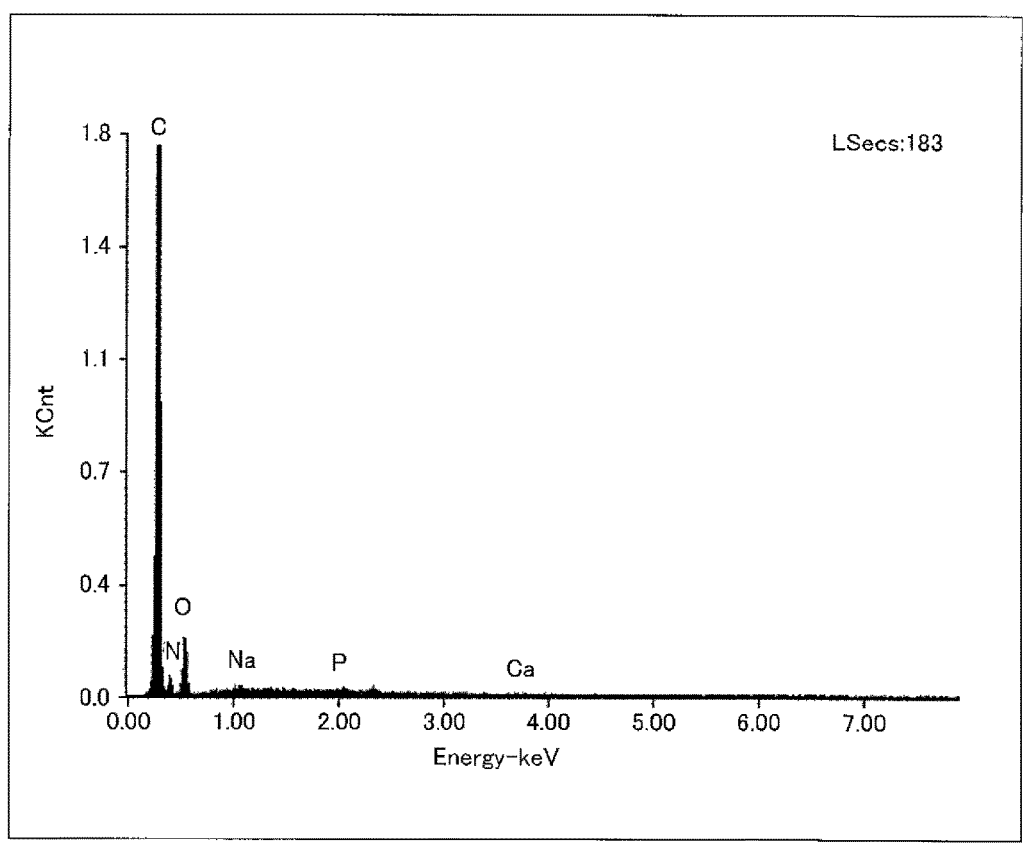
FIG. 10 shows a graph that shows a result of a cell elemental analysis in the case of using a commercially available culture plate which was not caused to be in contact with a degradation product of collagen.

FIGS. 8 through 10 each show a result of the elemental analysis. Specifically, FIG. 8 shows a result of an elemental analysis which was conducted in the case of using the commercially available culture plate caused to be in contact with the collagen degradation product described in <1> above, FIG. 9 shows a result of an elemental analysis which was conducted in the case of using the culture plate caused to be in contact with the commercially available and pepsin-treated type I collagen, and FIG. 10 shows a result of an elemental analysis which was conducted in the case of using the culture plate not caused to be in contact with a collagen degradation product.

As shown in FIG. 8, in the case of using the commercially available culture plate which was caused to be in contact with the collagen degradation product described in <1> above, an intense peak of each of "Ca" and "P" was observed. This shows that the collagen degradation product described in <1> above significantly promoted cell mineralization.

In addition to the peaks of "Ca" and "P," a peak of "Na" was also observed. This suggests that a product obtained from the cell mineralization was a bioapatite.

Meanwhile, as shown in FIG. 9, in the case of using the culture plate caused to be in contact with the commercially available and pepsin-treated type I collagen, a peak of each of "Ca" and "P" observed was only small. This shows that the commercially available and pepsin-treated type I collagen had a weak effect of promoting cell mineralization.

Further, as shown in FIG. 10, in the case of using the culture plate not caused to be in contact with a collagen degradation product, peaks of "Ca" and "P" were hardly observed. This shows that cell mineralization was not induced.

<15. Test Regarding Differentiation-Inducing Ability—4>

In this Example, osteogenesis ability in vivo of a collagen degradation product described in <1> above was tested. The following describes a test method and test results.

The planning of an animal experiment corresponding to the test and the feeding and managing of an experiment animal followed the regulations on animal experiment of Kindai University.

A rat (male, SPF, Kwl:SD, 12 weeks old) was anesthetized by an intraperitoneal injection of pentobarbital (Nembutal).

The body weight of the rat was measured. The body weight of the rat before implantation was approximately 400 g.

The rat was immobilized to an operating table and then a femoral region of the rat was shaved and disinfected.

The femoral region of the rat was given regional anesthesia by use of 4% xylocaine.

The femoral region of the rat was cut out to expose a bone. Specifically, the skin was separated from the meat in the femoral region by use of a scalpel and scissors. Subsequently, the periosteum was peeled off by use of tweezers and the scalpel and then the bone was exposed.

A hole with a diameter of 2.5 mm was formed in a part of an inner side of a tibia to which part the collateral ligament was attached. The hole had a depth which only allowed the hole to reach the cavitas medullaris instead of penetrating through the bone.

Into the hole, a freeze-dried collagen degradation product (approximately 2 mg to 3 mg) or ii) a mixture of a freeze-dried collagen degradation product (2 mg to 3 mg) and a rat bone marrow mesenchymal stem cell (a rat bone marrow mesenchymal stem cell which had been cultured in an osteogenesis culture medium for 1 day and then washed with PBS(−)) was disposed. As control tests, rats having no hole formed and rats having a hole formed but having nothing disposed in the hole were also prepared.

Note that the collagen degradation products used were a) a collagen degradation product described in <1> above or b) a commercially available and pepsin-treated type I collagen.

A muscular tissue under the skin was surgically closed at 3 to 5 locations.

The affected area was washed with PBS(−) containing an antibiotic to give a suppuration-preventing treatment to the rat.

The cut out skin was sutured, and then the affected area was disinfected.

After the anesthetic wore off, the rats were each kept isolated from one another. Each rat was kept in an environment under the condition of a room temperature of 23±2° C. and a humidity of 50% which were realized by use of an air conditioning system, and was fed with food and water ad libitum.

The rat was euthanized after being kept for 15 days.

The legs of the rat were fixed by use of a 10% formalin solution, and then a tissue near the above-described hole was subjected to hematoxylin-eosin staining (HE staining) in accordance with a well-known method.

Figure 11:
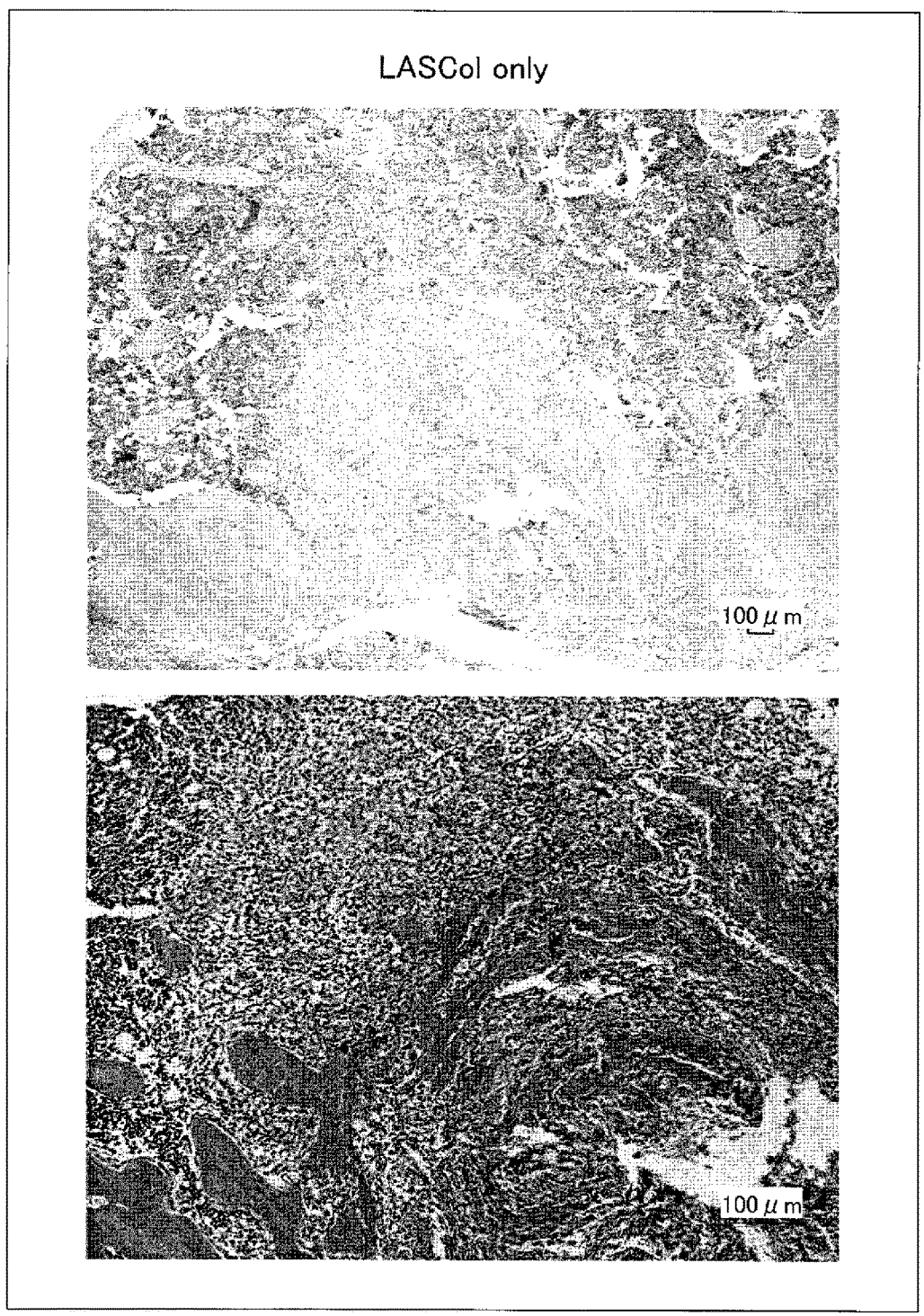
FIG. 11 shows photographs of the osteogenesis ability of a degradation product of collagen for the present invention.
Figure 12:
FIG. 12 shows photographs of the osteogenesis ability of a mixture of a degradation product of collagen for the present invention and rat bone marrow mesenchymal stem cells.
Figure 12:
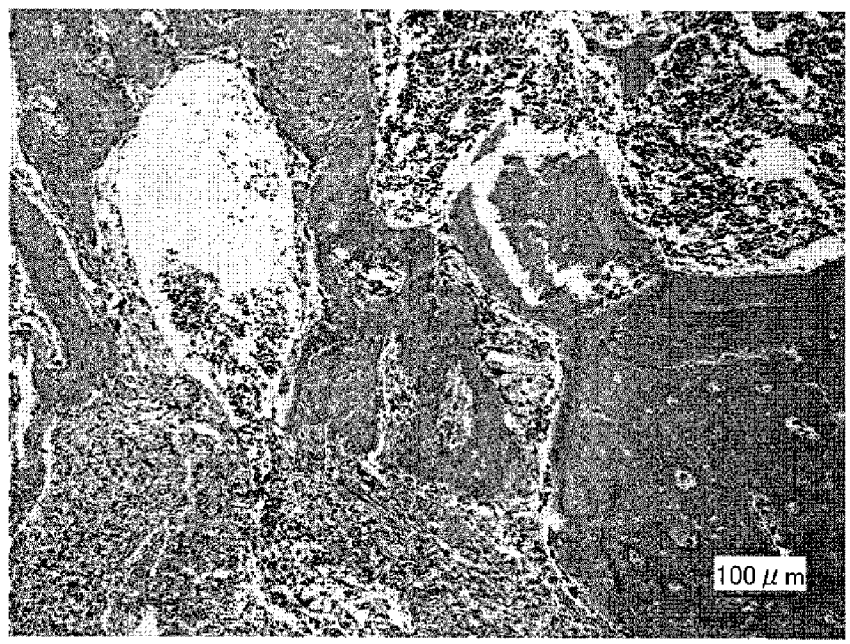
Figure 13:
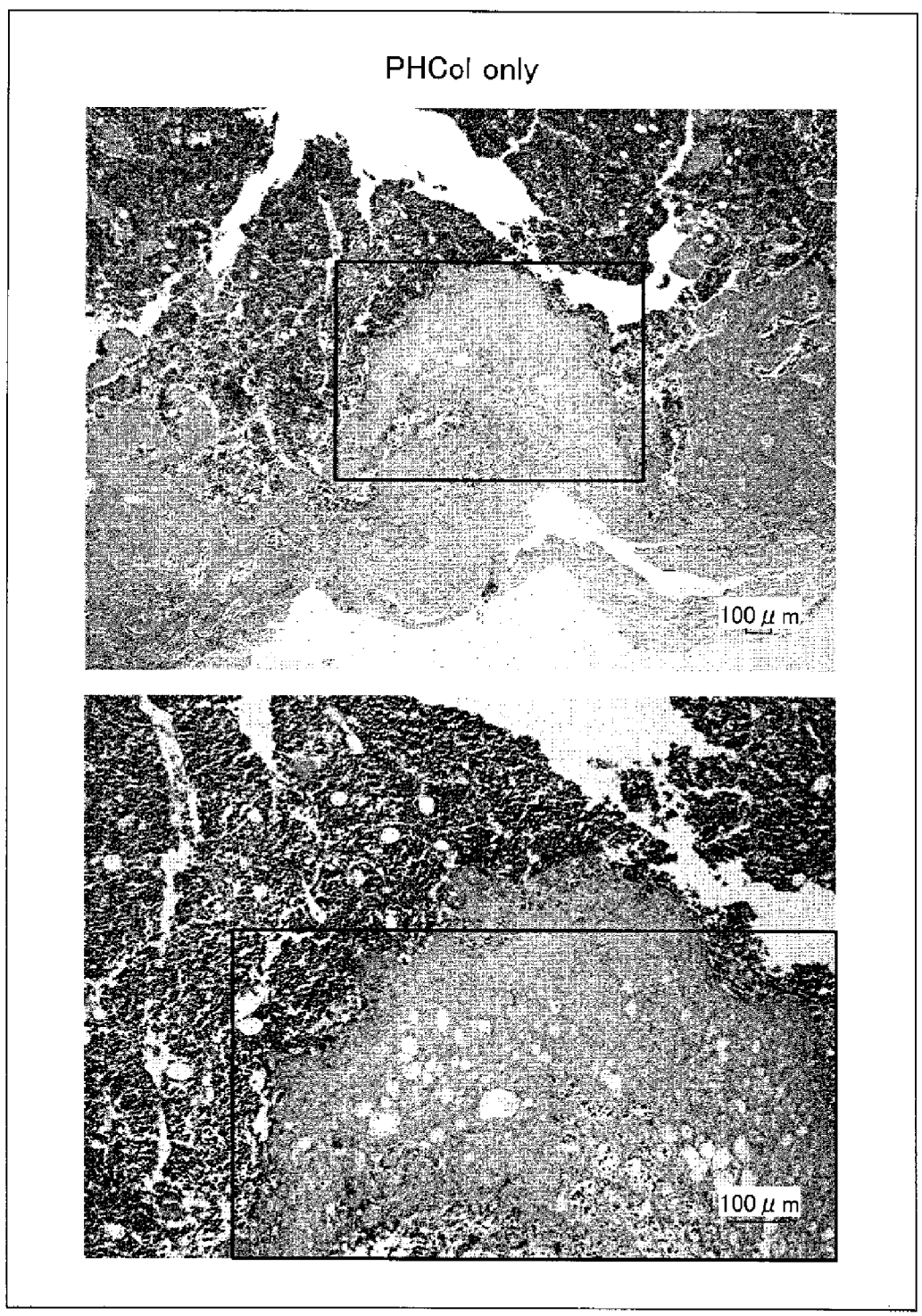
FIG. 13 shows photographs of the osteogenesis ability of a commercially available pepsin-treated type I collagen.
Figure 14:
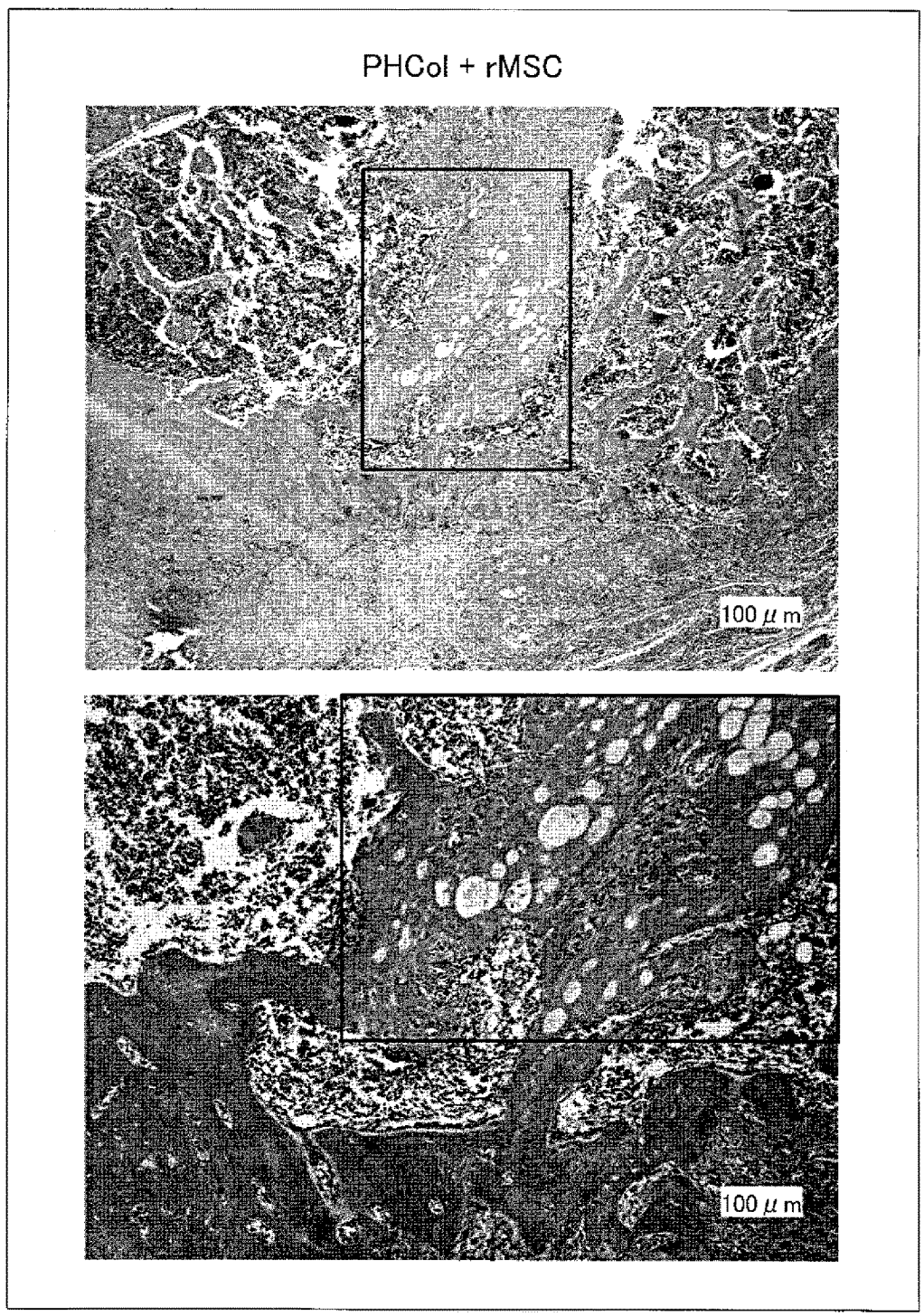
FIG. 14 shows photographs of the osteogenesis ability of a mixture of a commercially available pepsin-treated type I collagen and rat bone marrow mesenchymal stem cells.

Results of hematoxylin-eosin staining (HE staining) are shown in FIGS. 11 through 14. Specifically, FIG. 11 shows stained images in the case in which only the collagen degradation product described in <1> above was disposed in the hole, FIG. 12 shows stained images in the case in which the mixture of the collagen degradation product described in <1> above and the rat bone marrow mesenchymal stem cell was disposed in the hole, FIG. 13 shows stained images in the case in which only the commercially available and pepsin-treated type I collagen was disposed in the hole, and FIG. 14 shows stained images in the case in which the mixture of the commercially available and pepsin-treated type I collagen and the rat bone marrow mesenchymal stem cell was disposed in the hole.

As shown in FIGS. 11 and 12, in each of the case where "only the collagen degradation product described in <1> above" was disposed in the hole and the case where "the mixture of the collagen degradation product described in <1> above and the rat bone marrow mesenchymal stem cell" was disposed in the hole, the implanted collagen had disappeared by being absorbed by the living body and thus it was revealed that osteoanagenesis was induced well.

Note that as compared with the case where "only the collagen degradation product described in <1> above" was disposed in the hole, osteoanagenesis was induced better in the case where "the mixture of the collagen degradation product described in <1> above and the rat bone marrow mesenchymal stem cell" was disposed in the hole.

Meanwhile, as shown in FIGS. 13 and 14, in each of the case where "only the commercially available and pepsin-treated type I collagen" was disposed in the hole and the case where "the mixture of the commercially available and pepsin-treated type I collagen and the rat bone marrow mesenchymal stem cell" was disposed in the hole, the transplanted collagen remained in the hole (see, for example, sponge-like portions in the boxes in FIGS. 13 and 14), and thus it was revealed that osteoanagenesis was not induced well.

Table 11 below shows a body weight (A) of a rat before an implantation of a collagen degradation product, a body weight (B) of the rat after 15 days (immediately before euthanasia) from the implantation of the collagen degradation product, an amount (C) of increase in body weight, and a rate (D) of increase in body weight.

Note that in Table 11, "LASCol" shows a result obtained in the case in which only the collagen degradation product described in <1> above was disposed in the hole, "LASCol+rMSC" shows a result obtained in the case in which the mixture of the collagen degradation product described in <1> above and the rat bone marrow mesenchymal stem cell was disposed in the hole, "PHCol" shows a result obtained in the case in which only the commercially available and pepsin-treated type I collagen was disposed in the hole, and "Control" shows a result obtained in the case in which a hole was formed in the rat but nothing was disposed in the hole.

As shown in Table 11, the rates of increase in body weight of "LASCol" and "LASCol+rMSC" were approximately double the rates of increase in body weight of the other test results.

This suggests that the differentiation-inducing composition of this Example allows maintaining an amount of activity of and an amount of food ingested by a rat at healthy levels, and is very favorable due to inducing cell differentiation.

Further, an average amount of increase in body weight of a rat which was kept normally without having an operation was approximately 100 g during the test period, whereas an average amount of increase in body weight of rats of "LASCol" and "LASCol+rMSC" was 90 g, as shown in Table 11. This comparison also indicates that the differentiation-inducing composition of this Example allows maintaining an amount of activity of and an amount of food ingested by a rat at healthy levels, and allows a bone to heal extremely well.

<16. Test Regarding Differentiation-Inducing Ability—5>

A commercially available culture plate which was caused to be in contact with an above-described collagen degradation product (a pig-derived collagen degradation product obtained in a case of a salt concentration of 200 mM) was used in a test. A mouse fibroblast (NIH/3T3) was suspended in a 10% CS DMEM culture medium, and then was seeded in the culture plate above so as to be cultured under the condition of 37° C. and 5% $CO_2$.

Figure 15:
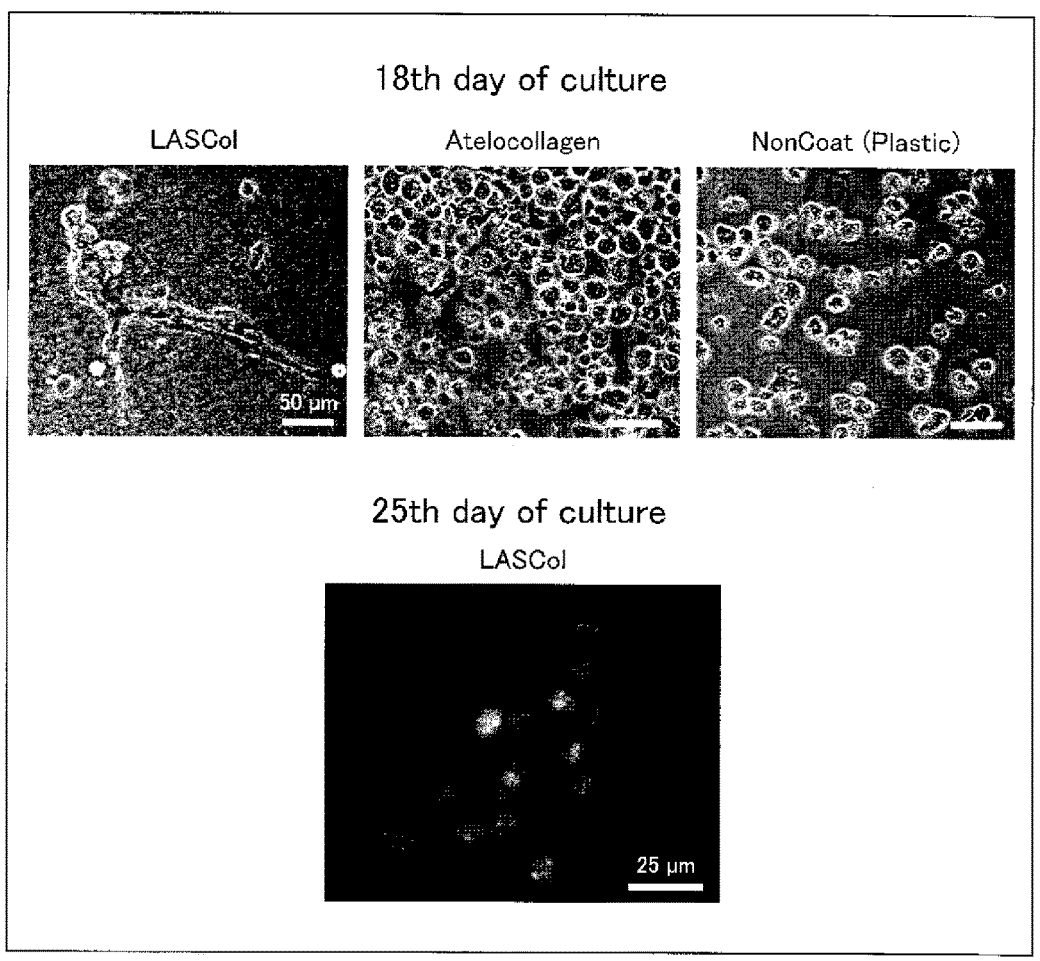
FIG. 15 shows photographs of a result of long-term cell culture in an Example of the present invention.

FIG. 15 shows test results. In FIG. 15, "LASCol" shows a result of the culture plate caused to be in contact with the collagen degradation product of this Example, "NonCoat (Plastic)" shows a result of a commercially available plastic plate, and "atelocollagen" shows a result of a commercially available and atelocollagen-coated plate.

As is clear from FIG. 15, after 18 days of culture, cells separated from an anchorage and shrunk to die in each of "atelocollagen" and "NonCoat(Plastic)." By contrast, cells of "LASCol" remained adhering to an anchorage and thus maintained a spheroid form.

After 25 days of culture, the nucleuses of cultured cells of "LASCol" were subjected to fluorescence stain by use of Hoechst 33342 (DOJINDO LABORATORIES) to check whether or not the cells were alive. A result thus obtained revealed that the collagen degradation product of this Example was suitable for long-term culture of cells.

A commercially available culture plate caused to be in contact with an above-described collagen degradation product (a pig-derived collagen degradation product obtained in a case of a salt concentration of 200 mM) was used in a test. Primary human mesenchymal stem cells (LONZA) were suspended in a growth medium (MSCBM+MSCGM, LONZA) dedicated for the cell, and then were seeded in the culture plate above so as to be cultured for 1 day under the condition of 37° C. and 5% $CO_2$. This caused the cells to adhere onto the culture plate.

After the cells adhered onto the culture plate, an entire amount of the culture medium was substituted with an osteoblast inducing culture medium (MSCGM, LONZA). Subsequently, the cells were cultured for 15 days under the condition of 37° C. and 5% $CO_2$ while the osteoblast inducing culture medium was substituted every 3 days. 15 days later, alkaline phosphatase (ALP) staining (Takara Bio Inc.) was conducted to examine the degree of differentiation of the primary human mesenchymal stem cells into osteoblasts.

Figure 16:
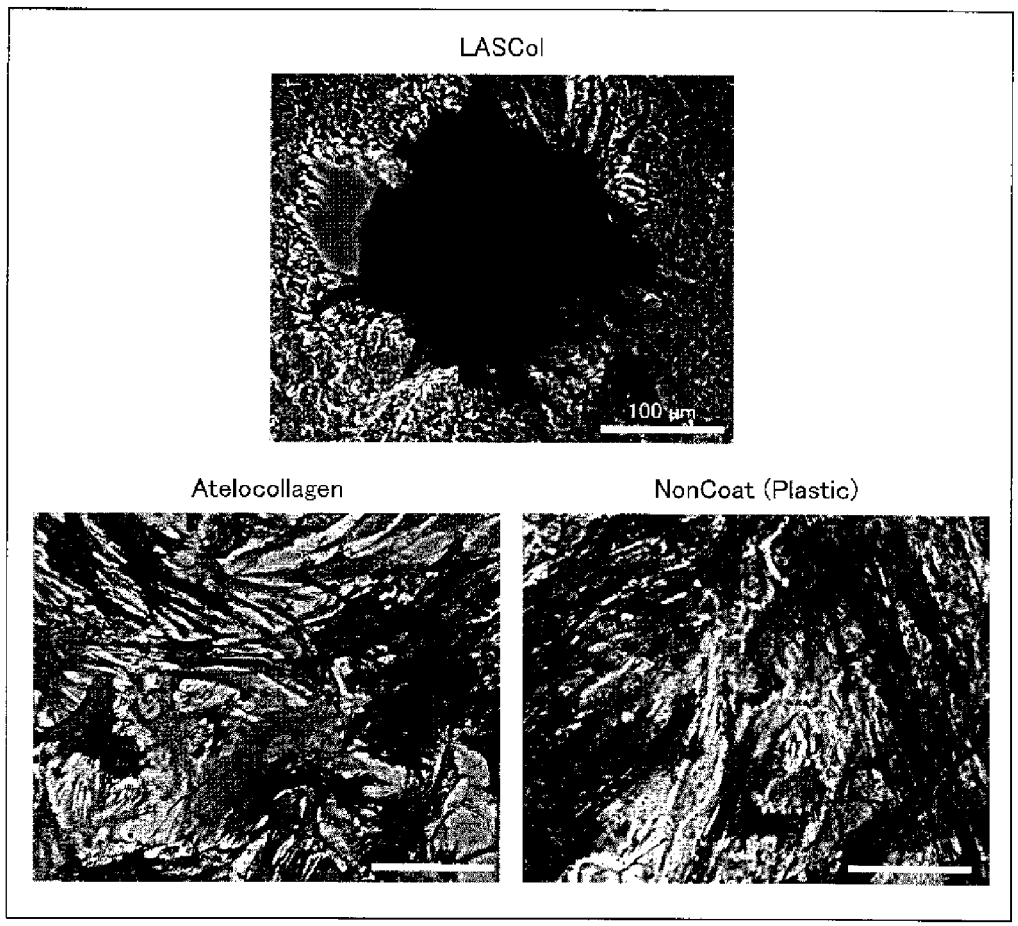
FIG. 16 shows photographs of a result of a test of inducing differentiation of human mesenchymal stem cells into a chondrocyte in an Example of the present invention.

FIG. 16 shows test results. In FIG. 16, "LASCol" shows a result of the culture plate caused to be in contact with the

TABLE 11

| Kind of sample | Rat No. | Body weight (g) Before enthesis A (g) | After enthesis B (g) | Increased amount C (g) (= B − A) | Average increased amount (g) | Increase rate D (%) (= C/A) | Average increase rate (%) | Average increase rate (%) |
|---|---|---|---|---|---|---|---|---|
| LASCol | 1 | 400 | 474 | 74 | 90 | 19 | 28 | 23 |
|  | 2 | 386 | 527 | 141 |  | 37 |  |  |
| LASCol + rMSC | 3 | 414 | 498 | 84 |  | 20 | 18 |  |
|  | 4 | 399 | 460 | 61 |  | 15 |  |  |
| PHCol | 5 | 392 | 445 | 53 | 46 | 14 | 12 | 11 |
|  | 6 | 430 | 473 | 43 |  | 10 |  |  |
| PHCol + rMSC | 7 | 391 | 429 | 38 |  | 10 | 11 |  |
|  | 8 | 425 | 476 | 51 |  | 12 |  |  |
| Control | 9 | 402 | 454 | 52 | 56 | 13 | 14 | 14 |
|  | 10 | 397 | 446 | 49 |  | 12 |  |  |
|  | 11 | 415 | 481 | 66 |  | 16 |  |  | collagen degradation product of this Example, "atelocollagen" shows a result of a commercially available and atelocollagen-coated plate, and "NonCoat(Plastic)" shows a result of a commercially available plastic plate. As is clear from FIG. 16, it was revealed that the collagen degradation product of this Example significantly promoted differentiation into an osteoblast.

A commercially available culture plate caused to be in contact with an above-described collagen degradation product (a pig-derived collagen degradation product obtained in a case of a salt concentration of 200 mM) was used in a test. Primary human mesenchymal stem cells (LONZA) were suspended in a growth medium (MSCBM+MSCGM, LONZA) dedicated for the cells, and then were seeded in the culture plate above so as to be cultured for 1 day under the condition of 37° C. and 5% $CO_2$. This caused the cells to adhere onto the culture plate.

After the cells adhered onto the culture plate, an entire amount of the culture medium was substituted with a chondrocyte inducing culture medium (GIBCO). Subsequently, the cells were cultured for 15 days under the condition of 37° C. and 5% $CO_2$ while the chondrocyte inducing culture medium was substituted every 3 days. 15 days later, a cartilage matrix produced by a cell was examined by Alcian blue staining (pH of 2.5) (Nacalai Tesque Inc., 37154-44).

Figure 17:
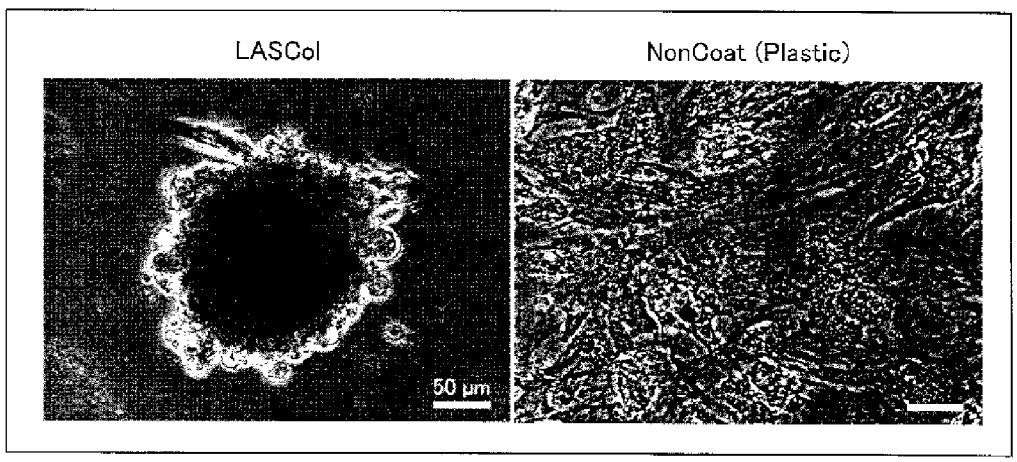
FIG. 17 shows photographs of a result of a test of inducing differentiation of human mesenchymal stem cells into a chondrocyte in an Example of the present invention.

FIG. 17 shows test results. In FIG. 17, "LASCol" shows a result of the culture plate caused to be in contact with the collagen degradation product of this Example, and "NonCoat(Plastic)" shows a result of a commercially available plastic plate. As is clear from FIG. 17, it was revealed that the collagen degradation product of this Example induced the primary human mesenchymal stem cells to spontaneously form a spheroid effective for chondrocyte differentiation and also promoted production of a cartilage matrix which was Alcian blue staining positive, which indicated differentiation into a chondrocyte.

A commercially available culture plate caused to be in contact with an above-described collagen degradation product (a pig-derived collagen degradation product obtained in a case of a salt concentration of 200 mM) was used in a test. Mouse MC3T3-G2/PA6 (RIKEN BRC) was suspended in a growth medium (10% FBS DMEM), and then was seeded in the culture plate above so as to be cultured for 1 day under the condition of 37° C. and 5% $CO_2$. This caused the cells to adhere onto the culture plate.

After the cells adhered onto the culture plate, an entire amount of the culture medium was substituted with a fresh culture medium (10% FBS DMEM). Subsequently, the cells were cultured for 6 days under the condition of 37° C. and 5% $CO_2$ while the culture medium was similarly substituted every 3 days.

Figure 18:
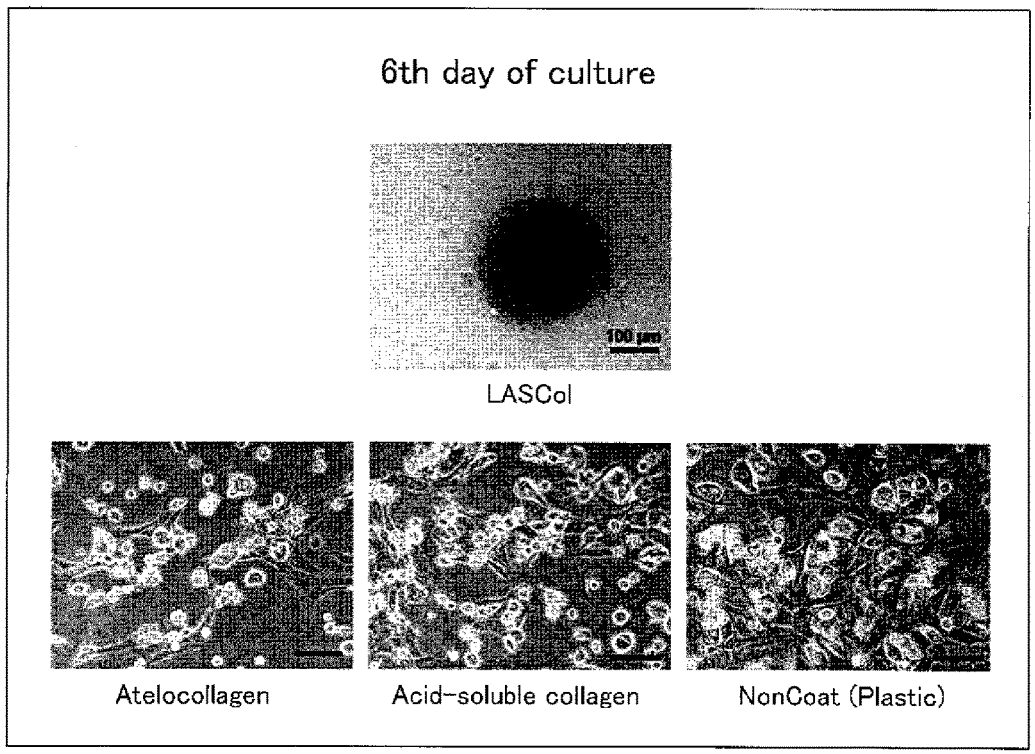
FIG. 18 shows photographs of a result of a test of inducing differentiation of mouse MC3T3-G2/PA6 cells into fat cells in an Example of the present invention.

FIG. 18 shows test results. In FIG. 18, "LASCol" shows a result of the culture plate caused to be in contact with the collagen degradation product of this Example, "atelocollagen" shows a result of a pepsin-treated collagen, "acid-soluble collagen" shows a collagen obtained from a tissue by acid extraction, and "NonCoat(Plastic)" shows a result of a commercially available plastic plate. As is clear from FIG. 18, it was revealed that in "LASCol," a spheroid effective for differentiation into a fat cell was spontaneously formed and the differentiation into the fat cell was thus promoted.

A commercially available culture plate caused to be in contact with an above-described collagen degradation product (a pig-derived collagen degradation product obtained in a case of a salt concentration of 200 mM) was used in a test. Rat C6 cells (RIKEN BRC) were suspended in a growth medium (10% FBS DMEM), and then were seeded in the culture plate above so as to be cultured under the condition of 37° C. and 5% $CO_2$. This caused the cells to adhere onto the culture plate.

Figure 19:
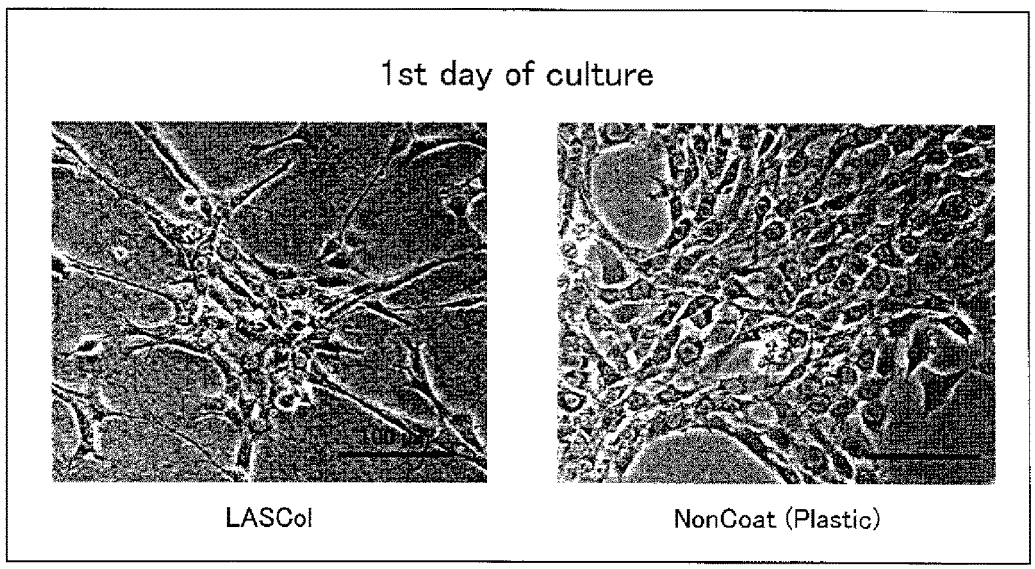
FIG. 19 shows photographs of a result of a test of inducing differentiation of C6 cells into glial cells in an Example of the present invention.

FIG. 19 shows test results. In FIG. 19, "LASCol" shows a result of the culture plate caused to be in contact with the collagen degradation product of this Example, and "NonCoat(Plastic)" shows a result of a commercially available plastic plate. As is clear from FIG. 19, it was revealed that in "LASCol," a cell process effective for differentiation into a glial cell was spontaneously formed and the differentiation into the glial cell was thus promoted.

A commercially available culture plate caused to be in contact with an above-described collagen degradation product (a pig-derived collagen degradation product obtained in a case of a salt concentration of 200 mM) was used in a test. Primary human mesenchymal stem cells (PromoCell) were suspended in a growth medium (Mesenchymal Stem Cell Growth Medium (C-28010), PromoCell) dedicated for the cells, and then were seeded in the culture plate above so as to be cultured for 2 days under the condition of 37° C. and 5% $CO_2$. This caused the cells to adhere onto the culture plate.

After 2 days of culture, an entire amount of the culture medium was substituted with a nerve cell inducing culture medium (Mesenchymal Stem Cell Neurogenic Differentiation Medium (Ready-to-use) (C-28015), PromoCell). Subsequently, the cells were cultured for 5 days under the condition of 37° C. and 5% $CO_2$ while the nerve cell inducing culture medium was substituted every 2 days. 5 days later, an intercellular network formed by neurite was observed by use of a phase difference microscope to examine the degree of differentiation of the primary human mesenchymal stem cells into nerve cells.

Figure 20:
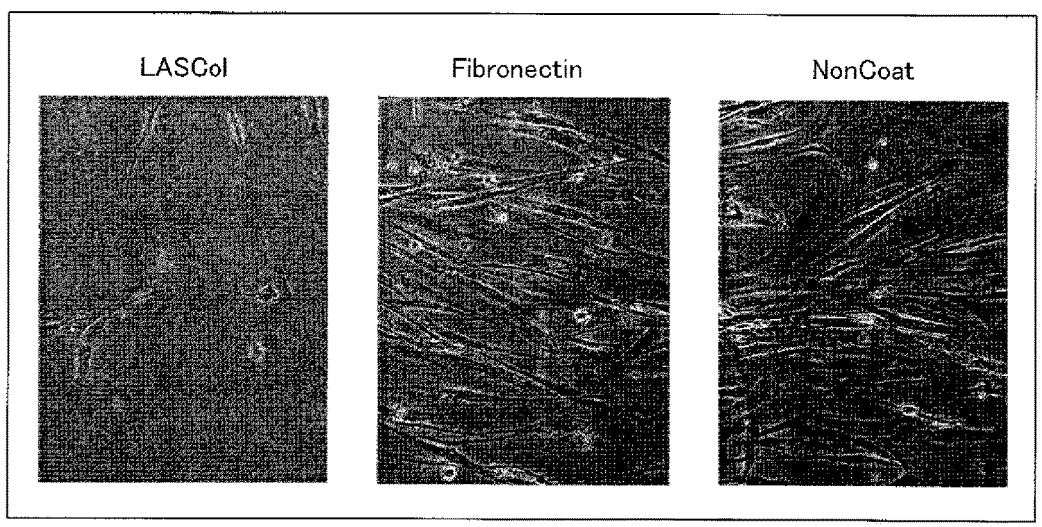
FIG. 20 shows photographs of a result of a test of inducing differentiation of human mesenchymal stem cells into nerve cells in an Example of the present invention.

FIG. 20 shows test results. In FIG. 20, "LASCol" shows a result of the culture plate caused to be in contact with the collagen degradation product of this Example, "fibronectin" shows a result of a commercially available plate to which fibronectin was applied in accordance with a manual, and "NonCoat(Plastic)" shows a result of a commercially available plastic plate. As is clear from FIG. 20, it was revealed that the collagen degradation product of this Example promoted differentiation into a nerve cell which constitutes a neurite network.

<17. Purification of Collagen from Bone>

Actinidain was supplied to a dialysis tube and was dialyzed against a dialysis outer liquid containing sodium chloride at a concentration of 2000 mM. Then, the dialysis outer liquid was substituted with distilled water and the dialysis was continued to obtain actinidain. Note that actinidain used had been purified by a well-known method (see, for example, Non Patent Literature 2). For activation of actinidain, actinidain was dissolved in a 50 mM phosphate buffer (pH of 6.5) containing 10 mM dithiothreitol, and a resultant aqueous solution was left to stand at 25° C. for 90 minutes.

Next, a buffer solution and a bone were mixed according to the following combinations (i) through (iii). That is, (i) a 50 mM citric acid buffer solution (pH of 3.0) containing a salt was mixed with a chicken ulna (45 mg (wet weight)), (ii) a 50 mM citric acid buffer solution (pH of 2.5 or 3.0) containing a salt was mixed with a pig tibia (20 mg (dry weight)), or (iii) a 50 mM acetic acid buffer solution (pH of 4.5, 5.0, or 5.5) containing a salt was mixed with a pig tibia (20 mg (dry weight)).

Each of the solutions of (i) to (iii) containing a bone was caused to be in contact with the aqueous solution containing actinidain at 20° C. for not shorter than 10 days to prepare a collagen degradation product.

As controls, a buffer solution and a bone were mixed according to the following combinations (iv) and (v). That is, (iv) a 50 mM citric acid buffer solution (pH of 3.0) which contained a salt and in which pig pepsin was dissolved was mixed with a chicken ulna (45 mg (wet weight)), and (v) a 50 mM citric acid buffer solution (pH of 3.0) which contained a salt and in which pig pepsin was dissolved was mixed with a pig tibia (20 mg (dry weight)).

Each of the solutions of (iv) and (v) containing a bone was caused to be in contact with the aqueous solution containing pig pepsin at 20° C. for not shorter than 7 days to prepare a collagen degradation product.

As a typical experimental example, when a weight of a collagen degradation product in a case of using actinidain under the condition of pH of 3.0 was measured, 18.5 mg of a collagen degradation product was successfully recovered from 45 mg (wet weight) of a chicken ulna (recovery rate 41%), and 15.4 mg of a collagen degradation product was successfully recovered from 20 mg (dry weight) of a pig tibia (recovery rate 77%).

Meanwhile, when a weight of a collagen degradation product in a case of using pig pepsin was measured, 1.7 mg of a collagen degradation product was successfully recovered from 45 mg (wet weight) of a chicken ulna (recovery rate 3.8%), and 0.2 mg of a collagen degradation product was recovered from 20 mg (dry weight) of a pig tibia (recovery rate 1.0%).

The difference in the recovery rates is significant. Further, it is assumed that a bone-derived solubilized collagen obtained by the method of this Example is used for a purpose equivalent to that of a dermis-derived collagen.

Bone and dentin are categorized as a hard tissue, and has been believed to be unsuitable as a raw material for recovering collagen or a collagen degradation product, unlike a soft tissue such as dermis and tendon. Conventionally, there has only been a method of conducting a heat denaturation treatment of a bone to extract gelatin from the bone, and there has been reported no method of extracting collagen having a triple stranded helix structure from a bone.

Surprisingly, however, the method of this Example allowed the solid content of a bone to dissolve entirely, so that a collagen degradation product and a bone matrix protein were successfully recovered in large quantities.

(a) and (b) of FIG. 21 show photographs each showing a case in which a bone fragment was caused to be in contact with enzymes and left to stand for 11 days. In a case where actinidain was used, there was observed no bone fragment which remained without being digested. By contrast, in a case where pepsin was used, there was observed a large bone fragment which remained without being digested.

A bone matrix protein contained in a degradation product was identified by peptide mass fingerprinting using a mass spectrometer. It was confirmed that such a bone-specific useful bone matrix protein (for example, osteocalcin etc.) other than collagen could also be recovered efficiently by solubilization of a bone tissue. The method of this Example thus allows preparing a degradation product containing a useful bone matrix protein. A bone which was submerged in a buffer solution to which no enzyme had been added was not solubilized at all, and the shape of a bone fragment did not change over time either.

Next, a collagen degradation product was transferred onto a PVDF (polyvinylidene difluoride) film by a normal method. Then, an amino acid sequence of an amino terminus of the degradation product transferred onto the PVDF film was determined by the Edman degradation technique.

Note that APRO Science Inc. or the analyzer collaboration laboratory of the Faculty of Medicine of Kindai University conducted the actual Edman analysis in accordance with a well-known method, at the request of the inventors.

As a result of the Edman analysis, it was revealed that among degradation products obtained, there was a degradation product in which an amino acid sequence of an amino terminus and the vicinity thereof corresponded to the amino acid sequence of SEQ ID NO: 14.

A commercially available culture plate which was caused to be in contact with a collagen degradation product (a pig tibia-derived collagen degradation product) prepared from a bone tissue was used in a test. Human bone marrow mesenchymal stem cells MSC were suspended in a growth medium (MSCGM) and then were seeded in the culture plate so as to be cultured for 1 day under the condition of 37° C. and 5% $CO_2$. This caused the cells to adhere onto the culture plate. FIG. 22 shows a fibroblast after the cells adhered onto the culture plate. As is clear from FIG. 22, the bone-derived collagen degradation product of this Example significantly promoted formation of a spheroid of the fibroblast.

INDUSTRIAL APPLICABILITY

The present invention is applicable to, for example, a differentiation-inducing composition, a food additive, a medical material, a cosmetic material, and a culture material for culturing a cell, embryo, or the like (for example, a coating material for a culture device [for example, a culture dish] and a culture medium component).

Sequence Listing

---

The invention claimed is:

1. A differentiation-inducing composition for inducing cell differentiation, the differentiation-inducing composition comprising:

a degradation product of a collagen or an atelocollagen, the degradation product containing at least a portion of a triple helical domain of the collagen or the atelocollagen, the degradation product resulting from:

cleavage of a chemical bond between $X_1$ and $X_2$, between $X_2$ and G, or between $X_4$ and G in an amino acid sequence in (1) below within the triple helical domain, cleavage of a chemical bond between $X_1$ and $X_2$, between $X_2$ and G, between $X_4$ and G, between G and $X_7$, or between $X_{14}$ and G in an amino acid sequence in (2) below within the triple helical domain, or cleavage of a chemical bond between $Y_1$ and $Y_2$ in an amino acid sequence in (3) below at an amino terminus of the triple helical domain, the amino acid sequence in (1) or (2) being at an amino terminus of the triple helical domain, a G in each of the amino acid sequences of (1) to (3) which G is at or closest to an amino terminus of the each of the amino acid sequwnces (1) to (3) being a G within a native triple helical domain which G is at or closest to an amino terminus of the native triple helical domain, (1) -G-$X_1$-$X_2$-G-$X_3$-$X_4$-G-$X_5$-$X_6$-G- (SEQ ID NO: 1), (2) -G-$X_1$-$X_2$-G-$X_3$-$X_4$-G-$X_5$-$X_6$-G-$X_7$-$X_8$-G-$X_9$-$X_{10}$-G-$X_{11}$-$X_{12}$-G-$X_{13}$-$X_{14}$-G (SEQ ID NO: 14), (3) -$Y_1$-$Y_2$-$Y_3$-G-$Y_4$-$Y_5$-G-$Y_6$-$Y_7$-G-$Y_8$-$Y_9$-G- (SEQ ID NO: 13), wherein G represents glycine, $X_1$ and $Y_4$ each represent proline, $X_2$ and $Y_5$ each represent methionine, $X_3$ and $Y_6$ each represent proline or leucine, $X_4$ and $Y_7$ each represent alanine or serine, $X_5$ and $Y_8$ each represent proline or serine, $X_6$ and $Y_9$ each represent arginine, and $X_7$ to $X_{14}$ and $Y_1$ to $Y_3$ each represent an amino acid.

2. The differentiation-inducing composition according to claim 1, wherein the cleavage in the amino acid sequence in (1), (2), or (3) is within at least one of an α1 chain and an α2 chain of the collagen or the atelocollagen.

* * * * *

SEQUENCE LISTING

```
<160> NUMBER OF SEQ ID NOS: 23

<210> SEQ ID NO 1
<211> LENGTH: 10
<212> TYPE: PRT
<213> ORGANISM: Artificial Sequence
<220> FEATURE:
<223> OTHER INFORMATION: Partial Sequence of Protein
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
```

```
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 1

Gly Xaa Xaa Gly Xaa Xaa Gly Xaa Xaa Gly
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Partial Sequence of Protein

<400> SEQUENCE: 2

Ile Ser Val Pro Gly Pro Met Gly Pro Ser Gly Pro Arg Gly
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Partial Sequence of Protein

<400> SEQUENCE: 3

Met Gly Pro Ser Gly Pro Arg Gly
1               5

<210> SEQ ID NO 4
<211> LENGTH: 16
<212> TYPE: PRT
<213> ORGANISM: Artificial Sequence
<220> FEATURE:
<223> OTHER INFORMATION: Partial Sequence of Protein

<400> SEQUENCE: 4

Ser Ala Gly Val Ser Val Pro Gly Pro Met Gly Pro Ser Gly Pro Arg
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Partial Sequence of Protein

<400> SEQUENCE: 5

Met Gly Pro Ser Gly Pro Arg
1               5

<210> SEQ ID NO 6
<211> LENGTH: 17
<212> TYPE: PRT
<213> ORGANISM: Artificial Sequence
<220> FEATURE:
<223> OTHER INFORMATION: Partial Sequence of Protein

<400> SEQUENCE: 6

Ser Ala Gly Val Ala Val Pro Gly Pro Met Gly Pro Ala Gly Pro Arg
1               5                   10                  15

Gly
```

-continued

```
<210> SEQ ID NO 7
<211> LENGTH: 7
<212> TYPE: PRT
<213> ORGANISM: Artificial Sequence
<220> FEATURE:
<223> OTHER INFORMATION: Partial Sequence of Protein

<400> SEQUENCE: 7

Gly Pro Ala Gly Pro Arg Gly
1               5

<210> SEQ ID NO 8
<211> LENGTH: 14
<212> TYPE: PRT
<213> ORGANISM: Artificial Sequence
<220> FEATURE:
<223> OTHER INFORMATION: Partial Sequence of Protein

<400> SEQUENCE: 8

Ile Ser Val Pro Gly Pro Met Gly Pro Ser Gly Pro Arg Gly
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Partial Sequence of Protein

<400> SEQUENCE: 9

Met Gly Pro Ser Gly Pro Arg Gly
1               5

<210> SEQ ID NO 10
<211> LENGTH: 29
<212> TYPE: PRT
<213> ORGANISM: Artificial Sequence
<220> FEATURE:
<223> OTHER INFORMATION: Partial Sequence of Protein

<400> SEQUENCE: 10

Ile Ser Val Pro Gly Pro Met Gly Pro Ser Gly Pro Arg Gly Leu Pro
1               5                   10                  15

Gly Pro Pro Gly Ala Pro Gly Pro Gln Gly Phe Gln Gly
            20                  25

<210> SEQ ID NO 11
<211> LENGTH: 16
<212> TYPE: PRT
<213> ORGANISM: Artificial Sequence
<220> FEATURE:
<223> OTHER INFORMATION: Partial Sequence of Protein

<400> SEQUENCE: 11

Gly Leu Pro Gly Pro Pro Gly Ala Pro Gly Pro Gln Gly Phe Gln Gly
1               5                   10                  15

<210> SEQ ID NO 12
<211> LENGTH: 4
<212> TYPE: PRT
<213> ORGANISM: Artificial Sequence
<220> FEATURE:
<223> OTHER INFORMATION: Partial Sequence of Protein

<400> SEQUENCE: 12

Gly Phe Gln Gly
1
```

```
<210> SEQ ID NO 13
<211> LENGTH: 13
<212> TYPE: PRT
<213> ORGANISM: Artificial Sequence
<220> FEATURE:
<223> OTHER INFORMATION: Partial Sequence of Protein
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 13

Xaa Xaa Xaa Gly Xaa Xaa Gly Xaa Xaa Gly Xaa Xaa Gly
1               5                   10

<210> SEQ ID NO 14
<211> LENGTH: 22
<212> TYPE: PRT
<213> ORGANISM: Artificial Sequence
<220> FEATURE:
<223> OTHER INFORMATION: Partial Sequence of Protein
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid

<400> SEQUENCE: 14

Gly Xaa Xaa Gly Xaa Xaa Gly Xaa Xaa Gly Xaa Xaa Gly Xaa Xaa Gly
1               5                   10                  15

Xaa Xaa Gly Xaa Xaa Gly
            20

<210> SEQ ID NO 15
<211> LENGTH: 15
<212> TYPE: PRT
<213> ORGANISM: Artificial Sequence
```

```
<220> FEATURE:
<223> OTHER INFORMATION: Partial Sequence of Protein

<400> SEQUENCE: 15

Leu Pro Gly Pro Pro Gly Ala Pro Gly Pro Gln Gly Phe Gln Gly
1               5                   10                  15

<210> SEQ ID NO 16
<211> LENGTH: 5
<212> TYPE: PRT
<213> ORGANISM: Artificial Sequence
<220> FEATURE:
<223> OTHER INFORMATION: Partial Sequence of Protein

<400> SEQUENCE: 16

Leu Pro Gly Pro Pro
1               5

<210> SEQ ID NO 17
<211> LENGTH: 21
<212> TYPE: PRT
<213> ORGANISM: Artificial Sequence
<220> FEATURE:
<223> OTHER INFORMATION: Partial Sequence of Protein

<400> SEQUENCE: 17

Met Ala Val Pro Gly Pro Met Gly Pro Met Gly Pro Arg Gly Ala Pro
1               5                   10                  15

Gly Pro Pro Gly Pro
            20

<210> SEQ ID NO 18
<211> LENGTH: 17
<212> TYPE: PRT
<213> ORGANISM: Artificial Sequence
<220> FEATURE:
<223> OTHER INFORMATION: Partial Sequence of Protein

<400> SEQUENCE: 18

Met Gly Pro Arg Gly Ala Pro Gly Pro Pro Gly Pro Ser Gly Pro Gln
1               5                   10                  15

Gly

<210> SEQ ID NO 19
<211> LENGTH: 5
<212> TYPE: PRT
<213> ORGANISM: Artificial Sequence
<220> FEATURE:
<223> OTHER INFORMATION: Partial Sequence of Protein

<400> SEQUENCE: 19

Ser Gly Pro Gln Gly
1               5

<210> SEQ ID NO 20
<211> LENGTH: 25
<212> TYPE: PRT
<213> ORGANISM: Artificial Sequence
<220> FEATURE:
<223> OTHER INFORMATION: Partial Sequence of Protein

<400> SEQUENCE: 20

Gln Tyr Asp Gly Lys Gly Val Gly Leu Gly Pro Gly Pro Met Gly Leu
1               5                   10                  15

Met Gly Pro Arg Gly Pro Pro Gly Ala
```

```
<210> SEQ ID NO 21
<211> LENGTH: 8
<212> TYPE: PRT
<213> ORGANISM: Artificial Sequence
<220> FEATURE:
<223> OTHER INFORMATION: Partial Sequence of Protein

<400> SEQUENCE: 21

Gly Pro Arg Gly Pro Pro Gly Ala
1               5

<210> SEQ ID NO 22
<211> LENGTH: 27
<212> TYPE: PRT
<213> ORGANISM: Artificial Sequence
<220> FEATURE:
<223> OTHER INFORMATION: Partial Sequence of Protein

<400> SEQUENCE: 22

Gln Tyr Asp Pro Ser Lys Ala Ala Asp Phe Gly Pro Gly Pro Met Gly
1               5                   10                  15

Leu Met Gly Pro Arg Gly Pro Pro Gly Ala Ser
            20                  25

<210> SEQ ID NO 23
<211> LENGTH: 9
<212> TYPE: PRT
<213> ORGANISM: Artificial Sequence
<220> FEATURE:
<223> OTHER INFORMATION: Partial Sequence of Protein

<400> SEQUENCE: 23

Gly Pro Arg Gly Pro Pro Gly Ala Ser
1               5
```